United States Patent
Bhavaraju et al.

(10) Patent No.: US 10,722,161 B2
(45) Date of Patent: Jul. 28, 2020

(54) IMPLANTABLE SENSOR DEVICES, SYSTEMS, AND METHODS

(71) Applicant: DexCom, Inc., San Diego, CA (US)

(72) Inventors: Naresh C. Bhavaraju, San Diego, CA (US); Sebastian Bohm, San Diego, CA (US); Robert J. Boock, Carlsbad, CA (US); Daiting Rong, San Diego, CA (US); Peter C. Simpson, Encinitas, CA (US)

(73) Assignee: DexCom, Inc., San Diego, CA (US)

( * ) Notice: Subject to any disclaimer, the term of this patent is extended or adjusted under 35 U.S.C. 154(b) by 696 days.

(21) Appl. No.: 13/836,260

(22) Filed: Mar. 15, 2013

(65) Prior Publication Data

US 2014/0005509 A1 Jan. 2, 2014

Related U.S. Application Data

(60) Provisional application No. 61/666,622, filed on Jun. 29, 2012, provisional application No. 61/666,625, (Continued)

(51) Int. Cl.
*A61B 5/00* (2006.01)
*A61B 5/1495* (2006.01)
(Continued)

(52) U.S. Cl.
CPC .......... *A61B 5/1495* (2013.01); *A61B 5/1459* (2013.01); *A61B 5/1473* (2013.01); *A61B 5/14532* (2013.01); *A61B 5/14865* (2013.01); *A61B 5/7221* (2013.01); *A61B 5/7246* (2013.01); *A61B 5/7278* (2013.01); *A61B 2562/04* (2013.01)

(58) Field of Classification Search
CPC . A61B 5/1495; A61B 5/7221; A61B 5/14865; A61B 5/1473; A61B 5/1459; A61B 5/7278; A61B 5/14532; A61B 5/7246; A61B 2562/04
See application file for complete search history.

(56) References Cited

U.S. PATENT DOCUMENTS 6,558,351 B1 5/2003 Steil et al.
6,560,471 B1 5/2003 Heller et al.
(Continued)

FOREIGN PATENT DOCUMENTS

WO  WO 2012/174563  12/2012

OTHER PUBLICATIONS

Klueh et al. (2011), J. Diab Sci Tech 5(3):583: Metabolic biofouling of glucose sensors in vivo: Role of tissue microhemorrhages.

*Primary Examiner* — Eric J Messersmith
(74) *Attorney, Agent, or Firm* — Knobbe, Martens, Olson & Bear, LLP

(57) ABSTRACT

Disclosed herein are devices, systems, and methods for a continuous analyte sensor, such as a continuous glucose sensor. In certain embodiments disclosed herein, various in vivo properties of the sensor's surroundings can be measured. In some embodiments, the measured properties can be used to identify a physiological response or condition in the body. This information can then be used by a patient, doctor, or system to respond appropriately to the identified condition.

14 Claims, 16 Drawing Sheets

Related U.S. Application Data filed on Jun. 29, 2012, provisional application No. 61/666,618, filed on Jun. 29, 2012.

(51) Int. Cl.
*A61B 5/1473* (2006.01)
*A61B 5/1459* (2006.01)
*A61B 5/145* (2006.01)
*A61B 5/1486* (2006.01)

(56) References Cited

U.S. PATENT DOCUMENTS

| | | | |
|---|---|---|---|
| 6,666,821 B2 * | 12/2003 | Keimel | A61B 5/14865 600/345 |
| 6,770,030 B1 * | 8/2004 | Schaupp et al. | 600/309 |
| 6,809,653 B1 | 10/2004 | Mann et al. | |
| 6,918,874 B1 | 7/2005 | Hatch et al. | |
| 9,974,472 B2 | 5/2018 | Hayter et al. | |
| 2005/0056552 A1 | 3/2005 | Simpson et al. | |
| 2005/0143635 A1 | 6/2005 | Kamath et al. | |
| 2007/0027370 A1 | 2/2007 | Brauker et al. | |
| 2007/0208246 A1 * | 9/2007 | Brauker et al. | 600/365 |
| 2007/0235331 A1 | 10/2007 | Simpson et al. | |
| 2007/0299617 A1 * | 12/2007 | Willis | 702/19 |
| 2008/0000779 A1 * | 1/2008 | Wang | A61B 5/14532 205/775 |
| 2008/0027287 A1 | 1/2008 | Shah et al. | |
| 2008/0076974 A1 | 3/2008 | Yamazaki et al. | |
| 2008/0161664 A1 | 7/2008 | Mastrototaro et al. | |
| 2008/0249385 A1 | 10/2008 | Phan et al. | |
| 2008/0287762 A1 * | 11/2008 | Hayter et al. | 600/365 |
| 2008/0300572 A1 | 12/2008 | Rankers et al. | |
| 2009/0018424 A1 | 1/2009 | Kamath et al. | |
| 2009/0023222 A1 | 1/2009 | Wu et al. | |
| 2009/0030641 A1 | 1/2009 | Fjield et al. | |
| 2009/0082693 A1 | 3/2009 | Stafford | |
| 2009/0105605 A1 | 4/2009 | Abreu et al. | |
| 2009/0131769 A1 * | 5/2009 | Leach et al. | 600/309 |
| 2009/0275815 A1 | 11/2009 | Bickoff et al. | |
| 2010/0219085 A1 | 9/2010 | Oviatt et al. | |
| 2010/0230285 A1 | 9/2010 | Hoss et al. | |
| 2010/0268304 A1 | 10/2010 | Matos | |
| 2010/0292557 A1 | 11/2010 | Pesach et al. | |
| 2011/0024307 A1 | 2/2011 | Simpson et al. | |
| 2011/0027127 A1 | 2/2011 | Simpson et al. | |
| 2011/0218489 A1 | 9/2011 | Mastrototaro et al. | |
| 2011/0237916 A1 | 9/2011 | Hanson et al. | |
| 2012/0028283 A1 | 2/2012 | Hoss et al. | |
| 2012/0078071 A1 | 3/2012 | Böhm et al. | |
| 2012/0097554 A1 | 4/2012 | Shah et al. | |
| 2012/0262298 A1 | 10/2012 | Böhm et al. | |
| 2012/0265035 A1 * | 10/2012 | Bohm et al. | 600/309 |
| 2013/0060105 A1 | 3/2013 | Shah et al. | |
| 2013/0112573 A1 | 5/2013 | Noble et al. | |
| 2013/0331673 A1 * | 12/2013 | Gautham | G01R 35/00 600/347 |
| 2014/0005505 A1 | 1/2014 | Peyser et al. | |
| 2014/0005508 A1 | 1/2014 | Estes et al. | |
| 2015/0090589 A1 | 4/2015 | Estes et al. | |

* cited by examiner

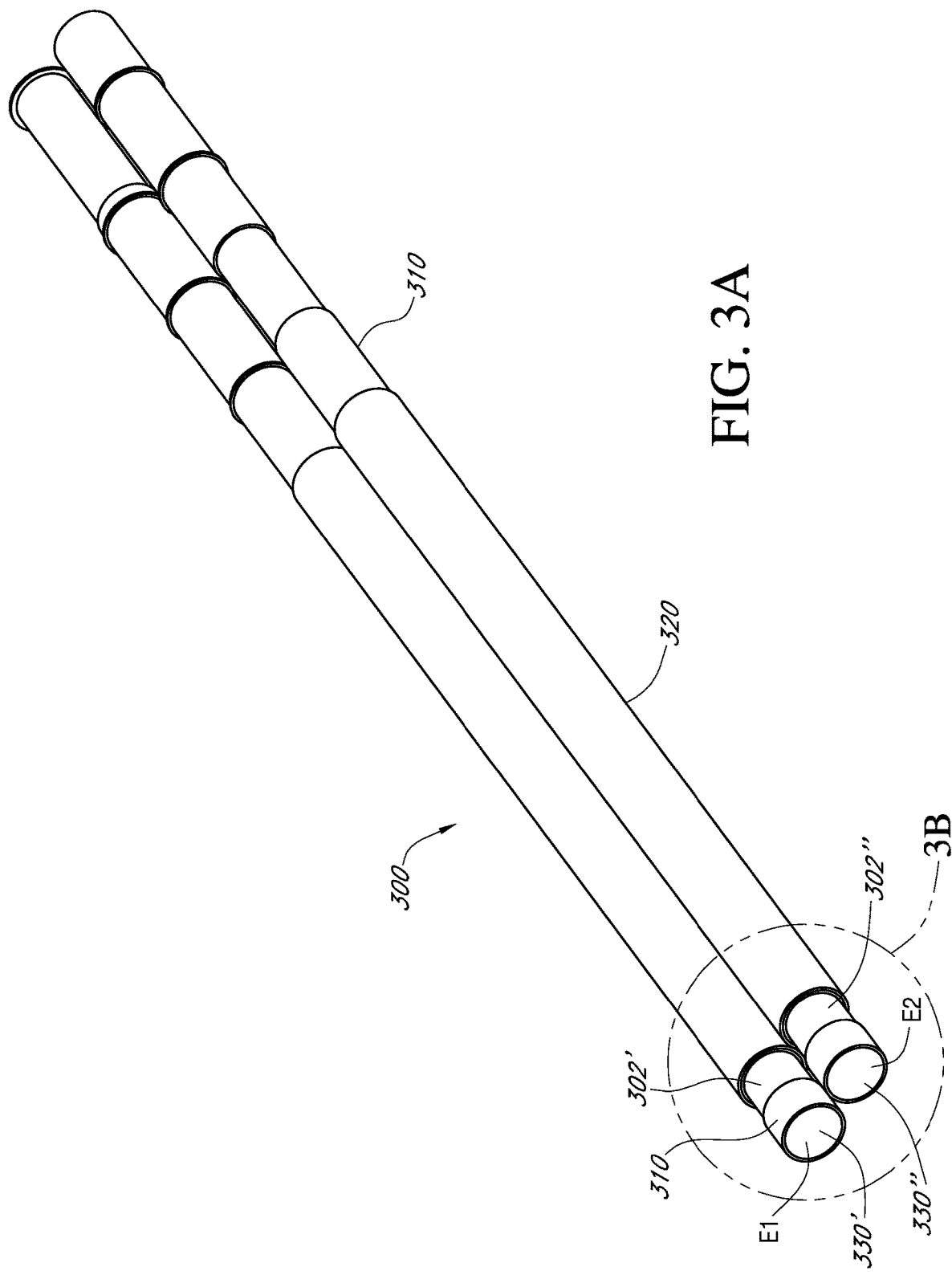

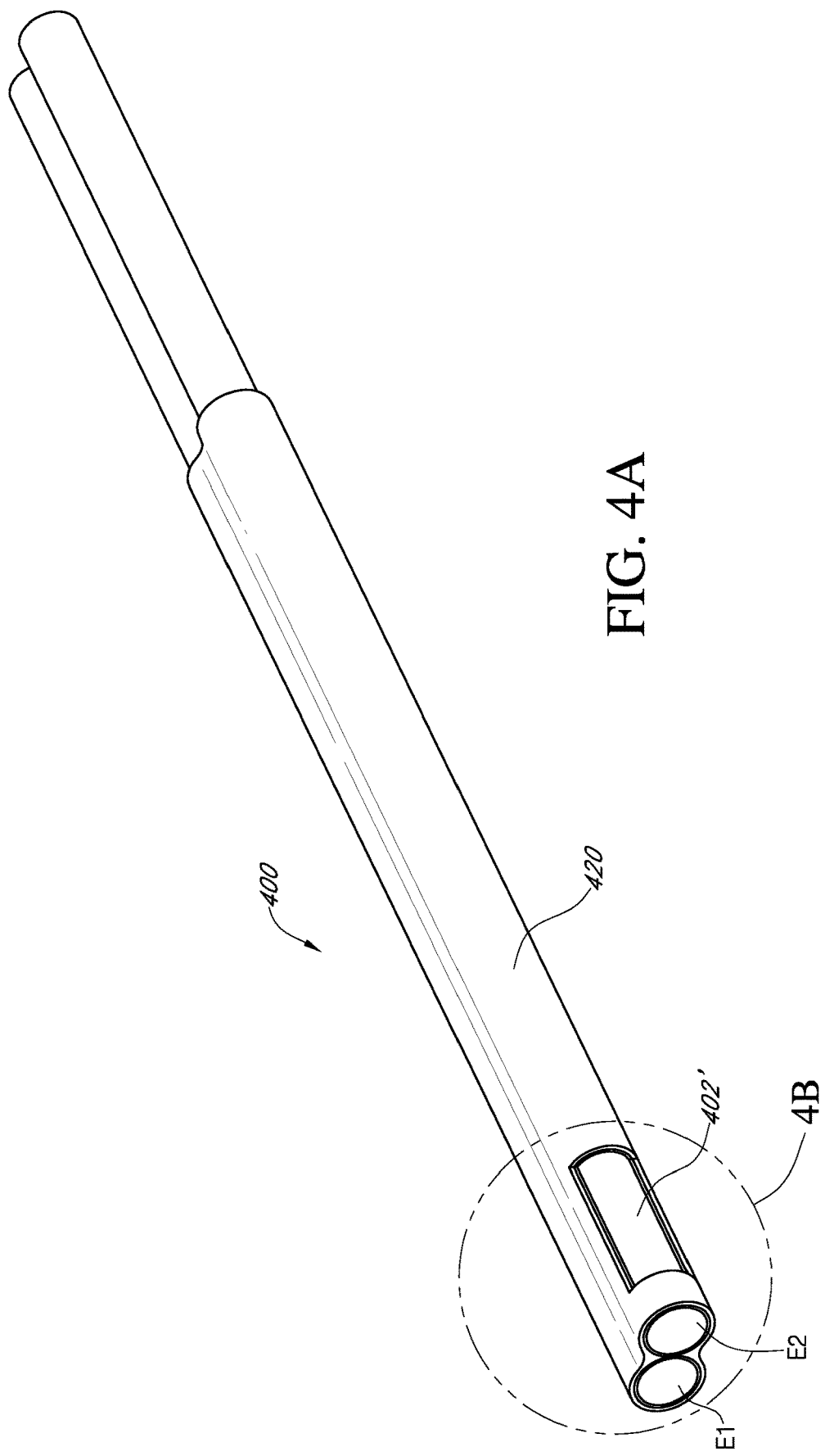

IMPLANTABLE SENSOR DEVICES, SYSTEMS, AND METHODS

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 61/666,622, filed Jun. 29, 2012, U.S. Provisional Application No. 61/666,625, filed Jun. 29, 2012, and U.S. Provisional Application No. 61/666,618, filed Jun. 29, 2012, the disclosures of which are hereby expressly incorporated by reference in their entirety and are hereby expressly made a portion of this application.

FIELD OF THE INVENTION

The embodiments described herein relate generally to devices, systems, and methods for measuring in vivo properties and identifying physiological changes in a host.

BACKGROUND OF THE INVENTION

Diabetes mellitus is a chronic disease which occurs when the pancreas does not produce enough insulin (Type I), or when the body cannot effectively use the insulin it produces (Type II). This condition typically leads to an increased concentration of glucose in the blood (hyperglycemia), which can cause an array of physiological derangements (such as, for example, kidney failure, skin ulcers, or bleeding into the vitreous of the eye) associated with the deterioration of small blood vessels. Sometimes, a hypoglycemic reaction (low blood sugar) is induced by an inadvertent overdose of insulin, or after a normal dose of insulin or glucose-lowering agent accompanied by extraordinary exercise or insufficient food intake.

Electrochemical sensors are useful in chemistry and medicine to determine the presence or concentration of a biological analyte. Such sensors are useful, for example, to monitor glucose in diabetic patients and lactate during critical care events. A variety of intravascular, transcutaneous and implantable sensors have been developed for continuously detecting and quantifying blood glucose values. Many conventional implantable glucose sensors suffer from complications within the body and provide only short-term or less-than-accurate sensing of blood glucose. Additionally, many conventional transcutaneous sensors have problems in accurately sensing and reporting back glucose or analyte values continuously over extended periods of time due to non-analyte-related signals caused by interfering species or unknown noise-causing events.

Specifically, transcutaneous and implantable sensors are affected by the in vivo properties and physiological responses in surrounding tissues. For example, a reduction in sensor accuracy following implantation of the sensor is one common phenomenon commonly observed. This phenomenon is sometimes referred to as an episode of "dip and recover." While not wishing to be bound by theory, dip and recover is believed to be triggered by trauma from insertion of the implantable sensor, and possibly from irritation of the nerve bundle near the implantation area, resulting in the nerve bundle reducing blood flow to the implantation area. Alternatively, dip and recover may be related to damage to nearby blood vessels, resulting in a vasospastic event. Any local cessation of blood flow in the implantation area for a period of time leads to a reduced amount of glucose in the area of the sensor. During this time, the sensor has a reduced sensitivity and is unable to accurately track glucose. Thus, dip and recover manifests as a suppressed glucose signal. The suppressed signal from dip and recover often appears within the first day after implantation of the signal, most commonly within the first 12 hours after implantation. Typically, dip and recover will resolve itself within 6-8 hours. Identification of dip and recover can provide information to a patient, physician, or other user that the sensor is only temporarily affected by a short-term physiological response, and that there is no need to remove the implant as normal function will likely return within hours.

Other physiological responses to the implantable sensor can also affect performance of the implantable sensor. For example, during wound healing and foreign body response, the surface of the implantable sensor can become coated in protein or other biological material to such an extent that the sensor is unable to accurately track blood glucose. This phenomenon is sometimes called "biofouling," and biofouling often manifests itself as a downward shift in sensor sensitivity over time. Similarly, the implantable sensor can become encapsulated by biological material to such an extent that the sensor is unable to provide glucose data, and the sensor is considered to effectively be at end of life. In some cases, the implantable device can be programmed to correct for errors associated with biofouling and end of life, so that identification of these phenomenon aids in providing more accurate glucose data. Identification of these phenomena also generally indicates that the device should be replaced.

Other efforts have been made to obtain blood glucose data from implantable devices and retrospectively determine blood glucose trends for analysis; however, so far these efforts have not adequately identified and compensated for in vivo physiological changes and have not aided the patient in determining reliable real-time blood glucose information.

SUMMARY OF THE INVENTION

In order to obtain more reliable blood glucose data, improved sensors and systems that can measure, identify, and respond to various in vivo properties and physiological responses are needed.

Accordingly, in a first aspect a method is provided for processing data from a continuous glucose sensor, the method comprising: receiving sensor data generated by a continuous glucose sensor, wherein the sensor data is indicative of a concentration of glucose in a host; identifying, using a processor module, a post-implantation transient loss of sensitivity of the continuous glucose sensor; and processing the sensor data, using the processor module, responsive to the identification of the loss of sensitivity.

In an embodiment of the first aspect, the sensor data comprises data indicative of a signal response to at least one event selected from the group consisting of a signal response to cessation of blood flow to a site surrounding sensor implantation, a signal response to reduction of blood flow to a site surrounding sensor implantation, and a signal response to a vasospastic event.

In an embodiment of the first aspect, identifying the post-implantation transient loss of sensitivity comprises determining a severity of the loss of sensitivity.

In an embodiment of the first aspect, processing the sensor data is performed based on the severity of the loss of sensitivity.

In an embodiment of the first aspect, identifying the post-implantation transient loss of sensitivity comprises: deactivating the continuous glucose sensor for a time period, whereby a product from a catalyzed reaction of glucose and oxygen accumulates over the time period; activating the continuous glucose sensor and measuring a signal value of the continuous glucose sensor immediately after the time period; and determining an occurrence of a post-implantation transient loss of sensitivity event if the signal value is greater than a predetermined value.

In an embodiment of the first aspect, the continuous glucose sensor comprises a first electrode and a second electrode, and wherein identifying the post-implantation transient loss of sensitivity comprises: measuring a stimulus signal passed across the first electrode and the second electrode; and determining an occurrence of a post-implantation transient loss of sensitivity event if the measured stimulus signal is greater or less than a predetermined value.

In an embodiment of the first aspect, the stimulus signal measured is impedance.

In an embodiment of the first aspect, identifying the post-implantation transient loss of sensitivity comprises determining a pH of a biological fluid surrounding the continuous glucose sensor.

In an embodiment of the first aspect, identifying the post-implantation transient loss of sensitivity comprises: measuring a concentration value of a non-glucose analyte; and determining an occurrence of a post-implantation transient loss of sensitivity event if the concentration value of the non-glucose analyte changes more than a predetermined amount.

In an embodiment of the first aspect, the method further comprises responding to an occurrence of a post-implantation transient loss of sensitivity event.

In an embodiment of the first aspect, responding comprises releasing a bio-active agent configured to minimize reduction or cessation of blood flow to a site surrounding sensor implantation.

In an embodiment of the first aspect, the continuous glucose sensor comprises a first electrode and a second electrode.

In an embodiment of the first aspect, the first electrode and second electrode have different dimensions.

In an embodiment of the first aspect, the second electrode is configured to have a dimension that positions the second electrode post-implantation outside of a site affected by cessation or reduction of blood flow.

In an embodiment of the first aspect, at least one of the first electrode and the second electrode is configured to minimize tissue trauma from implantation.

In an embodiment of the first aspect, the method further comprises: determining that the second electrode is positioned outside of a site affected by cessation or reduction of blood flow; and wherein processing the sensor data responsive to the identification of the loss of sensitivity comprises according more weight to sensor data generated by the second electrode than sensor data generated by the first electrode.

In an embodiment of the first aspect, the continuous glucose sensor comprises a first electrode configured to generate a first signal and a second electrode configured to generate a second signal, and wherein identifying the post-implantation transient loss of sensitivity of the continuous glucose sensor comprises: evaluating a difference between the first signal with the second signal; and recognizing a similarity between the difference and a pattern indicative of post-implantation transient loss of sensitivity.

In an embodiment of the first aspect, the first electrode and the second electrode are substantially collocated.

In an embodiment of the first aspect, the first electrode and the second electrode are separated by a distance greater than 1 mm.

In a second aspect, a method is provided for processing data from a continuous glucose sensor, the method comprising: receiving sensor data generated by a continuous glucose sensor configured to be implanted in a subcutaneous tissue of a host and to measure a glucose concentration therein, the continuous glucose sensor comprising: at least one electrode operatively connected to electronic circuitry configured to generate a signal representative of a concentration of glucose in a host; and at least one membrane located over at least a portion of the at least one electrode; identifying, using a processor module, a post-implantation loss of sensitivity of the continuous glucose sensor due to accumulation of biological material on the membrane; and processing the sensor data, using the processor module, responsive to the identification of the loss of sensitivity.

In an embodiment of the second aspect, the at least one electrode comprises a first electrode and a second electrode and the at least one membrane comprises a first membrane covering at least a portion of the first electrode and a second membrane covering at least a portion of the second electrode.

In an embodiment of the second aspect, the first membrane is enzymatic and comprises an enzyme configured to catalyze a reaction of glucose and oxygen from a biological fluid surrounding the membrane and the second membrane is non-enzymatic.

In an embodiment of the second aspect, identifying a post-implantation loss of sensitivity comprises: measuring a stimulus signal passed across the first electrode and the second electrode; and determining an occurrence of a post-implantation loss of sensitivity event if the measured stimulus signal is greater or less than a predetermined value.

In an embodiment of the second aspect, the stimulus signal measured is impedance.

In an embodiment of the second aspect, the method further comprises comparing sensor data generated by the first electrode with sensor data generated by the second electrode.

In an embodiment of the second aspect, identifying the post-implantation loss of sensitivity comprises: measuring a concentration value of a non-glucose analyte; and determining an occurrence of a post-implantation transient loss of sensitivity event if the concentration value of the non-glucose analyte changes more than a predetermined amount.

In an embodiment of the second aspect, identifying the post-implantation loss of sensitivity comprises determining a severity of the loss of sensitivity.

In an embodiment of the second aspect, processing the sensor data is performed based on the severity of the loss of sensitivity.

In an embodiment of the second aspect, the method further comprises responding to an occurrence of a post-implantation loss of sensitivity event.

In an embodiment of the second aspect, responding comprises releasing a bioactive agent configured to break down and/or remove the biological material on the membrane.

In an embodiment of the second aspect, the bioactive agent comprises an enzyme configured to react with the biological material.

In an embodiment of the second aspect, responding comprises agitating the at least one electrode and/or the at least one membrane, whereby at least a portion of the biological material is dislodged from the membrane.

In an embodiment of the second aspect, agitating is at least one of mechanically agitating or ultrasonically agitating.

In an embodiment of the second aspect, the first membrane is configured to be more susceptible to biofouling than the second membrane, and wherein processing the sensor data responsive to the identification of the post-implantation loss of sensitivity comprises according more weight to sensor data generated by the second electrode than to sensor data generated by the first electrode.

In a third aspect, a method for processing data from a continuous glucose sensor, the method comprising: receiving sensor data generated by a continuous glucose sensor configured to be implanted in a subcutaneous tissue of a host and to measure a glucose concentration therein, the continuous glucose sensor comprising: at least one electrode operatively connected to electronic circuitry configured to generate a signal representative of a concentration of glucose in a host; and at least one membrane located over at least a portion of the at least one electrode; identifying, using a processor module, a post-implantation loss of sensitivity of the continuous glucose sensor due to a biological encapsulation of at least a portion of the continuous glucose sensor; and processing the sensor data, using the processor module, responsive to the identification of the loss of sensitivity.

In an embodiment of the third aspect, the at least one electrode comprises a first electrode and a second electrode, and wherein the at least one membrane comprises a first membrane covering at least a portion of the first electrode and a second membrane covering at least a portion of the second electrode.

In an embodiment of the third aspect, a first continuous glucose sensor, formed at least in part by the first electrode and the first membrane, is configured to be more sensitive to glucose than a second continuous glucose sensor, formed at least in part by the second electrode and second membrane.

In an embodiment of the third aspect, the first continuous glucose sensor is configured to be more susceptible to the post-implantation loss of sensitivity than the second continuous glucose sensor.

In an embodiment of the third aspect, the method further comprises: determining that the second continuous glucose sensor is not experiencing post-implantation loss of sensitivity and that the first continuous glucose sensor is experiencing post-implantation loss of sensitivity; and wherein processing the sensor data responsive to the identification of the loss of sensitivity comprises according more weight to sensor data generated by the second electrode than to sensor data generated by the first electrode.

In an embodiment of the third aspect, identifying the post-implantation loss of sensitivity comprises: measuring an oxygen concentration of the biological fluid surrounded by the encapsulation; and determining an occurrence of a post-implantation loss of sensitivity event if the measured oxygen concentration is less than a predetermined value.

In an embodiment of the third aspect, identifying the post-implantation loss of sensitivity comprises: deactivating the continuous glucose sensor for a time period, whereby a product from a catalyzed reaction of glucose and oxygen accumulates over the time period; activating the continuous glucose sensor and measuring a signal value of the continuous glucose sensor immediately after the time period; and determining an occurrence of a post-implantation loss of sensitivity event if the signal value is greater than a predetermined value.

In an embodiment of the third aspect, identifying the post-implantation loss of sensitivity comprises: measuring a concentration value of a non-glucose analyte; and determining an occurrence of a post-implantation transient loss of sensitivity event if the concentration value of the non-glucose analyte changes more than a predetermined amount.

In an embodiment of the third aspect, identifying the post-implantation loss of sensitivity comprises determining a severity of the loss of sensitivity.

In an embodiment of the third aspect, processing the sensor data is performed based on the severity of the loss of sensitivity.

In an embodiment of the third aspect, the method further comprises responding to an occurrence of a post-implantation loss of sensitivity event.

In an embodiment of the third aspect, responding comprises moving the continuous glucose sensor to a different location outside the encapsulation.

In an embodiment of the third aspect, responding comprises releasing a bioactive agent configured to break down and/or remove the biological encapsulation.

In an embodiment of the third aspect, the method further comprises sending an alert that an end of the sensor's life is near.

In an embodiment of the third aspect, the at least one electrode comprises a first electrode configured to generate a first signal and a second electrode configured to generate a second signal, and wherein identifying the post-implantation loss of sensitivity comprises: evaluating a difference between the first signal with the second signal; and recognizing a similarity between the difference and a pattern indicative of post-implantation loss of sensitivity.

In an embodiment of the third aspect, the pattern comprises a substantially vacillating first signal and a substantially steady second signal.

In an embodiment of the third aspect, the first electrode and the second electrode are substantially collocated.

In an embodiment of the third aspect, the first electrode and the second electrode are separated by a distance greater than 1 mm.

Any embodiment of the first aspect may be employed in combination with any one or more of the other embodiments of the first aspect. Any embodiment of the second aspect may be employed in combination with any one or more of the other embodiments of the second aspect. Any embodiment of the third aspect may be employed in combination with any one or more of the other embodiments of the third aspect. Likewise, any one or more of the methods of the first and/or second and/or third aspects and/or their associated embodiments may be employed with any other one or more of the methods of the first and/or second and/or third aspects and/or their associated embodiments.

BRIEF DESCRIPTION OF THE DRAWINGS

These and other features and advantages will be appreciated, as they become better understood by reference to the following detailed description when considered in connection with the accompanying drawings, wherein:

FIG. 3A is a perspective-view schematic illustrating an in vivo portion of a multi-electrode analyte sensor, in another embodiment.

FIG. 4A is a perspective-view schematic illustrating an in vivo portion of a multi-electrode analyte sensor, in another embodiment.

DETAILED DESCRIPTION OF THE PREFERRED EMBODIMENTS

Definitions

Figure 1:
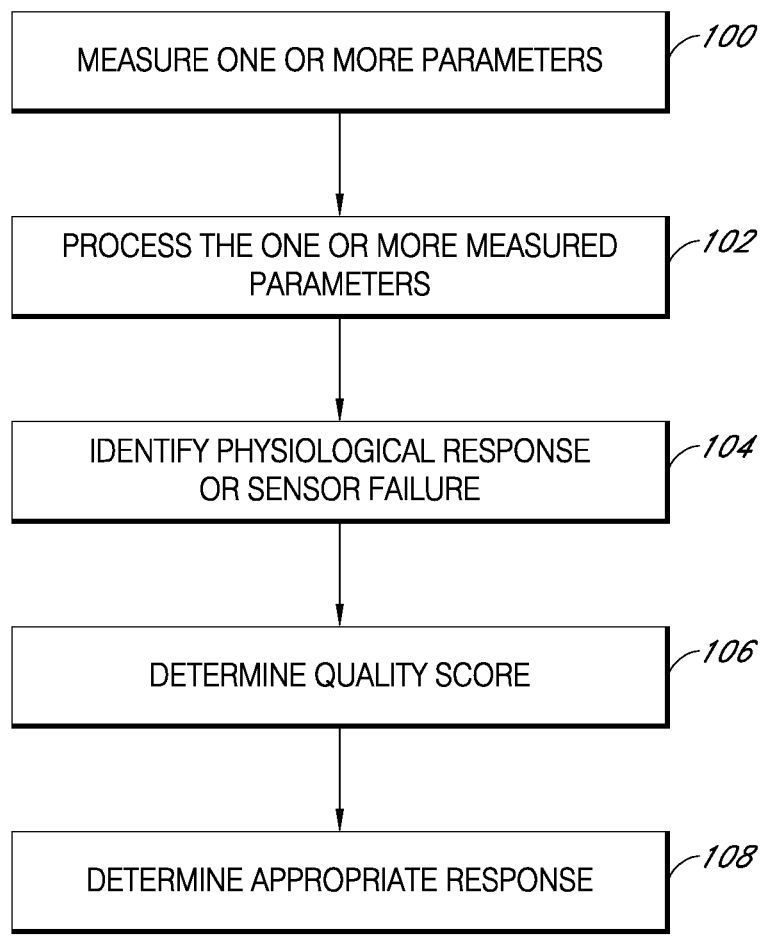
FIG. 1 is a flowchart illustrating a process of measuring, identifying, and responding steps, in accordance with one embodiment.

In order to facilitate an understanding of the embodiments described herein, a number of terms are defined below.

The term "about," as used herein, is a broad term, and is to be given its ordinary and customary meaning to a person of ordinary skill in the art (and is not to be limited to a special or customized meaning), and when associated with any numerical values or ranges, refers without limitation to the understanding that the amount or condition the terms modify can vary some beyond the stated amount so long as the function of the embodiment is realized.

The term "A/D Converter," as used herein, is a broad term, and is to be given its ordinary and customary meaning to a person of ordinary skill in the art (and is not to be limited to a special or customized meaning), and refers without limitation to hardware and/or software that converts analog electrical signals into corresponding digital signals.

The term "analyte," as used herein, is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies, A, S, C, E, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free B-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, rickettsia (scrub typhus), *Schistosoma mansoni, Toxoplasma gondii, Trepenoma pallidium, Trypanosoma cruzi/rangeli,* vesicular stomatis virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "baseline," as used herein is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation $y=mx+b$, the value of b represents the baseline of the signal. In certain embodiments, the value of b (i.e., the baseline) can be zero or about zero. This can be the result of a baseline-subtracting electrode or low bias potential settings, for example. As a result, for these embodiments, calibration can be defined by solving for the equation $y=mx$.

The term "biological sample," as used herein, is a broad term, and is to be given its ordinary and customary meaning to a person of ordinary skill in the art (and is not to be limited to a special or customized meaning), and refers without limitation to sample derived from the body or tissue of a host, such as, for example, blood, interstitial fluid, spinal fluid, saliva, urine, tears, sweat, or other like fluids.

The term "calibration," as used herein, is a broad term, and is to be given its ordinary and customary meaning to a person of ordinary skill in the art (and is not to be limited to a special or customized meaning), and refers without limitation to the process of determining the graduation of a sensor giving quantitative measurements (e.g., analyte concentration). As an example, calibration may be updated or recalibrated over time to account for changes associated with the sensor, such as changes in sensor sensitivity and sensor background. In addition, calibration of the sensor can involve, automatic, self-calibration, that is, calibration without using reference analyte values after point of use.

The term "co-analyte" as used herein is a broad term, and is to be given its ordinary and customary meaning to a person of ordinary skill in the art (and it is not to be limited to a special or customized meaning), and refers without limitation to a molecule required in an enzymatic reaction to react with the analyte and the enzyme to form the specific product being measured. In one embodiment of a glucose sensor, an enzyme, glucose oxidase (GOX) is provided to react with glucose and oxygen (the co-analyte) to form hydrogen peroxide.

The term "comprising" as used herein is synonymous with "including," "containing," or "characterized by," and is inclusive or open-ended and does not exclude additional, unrecited elements or method steps.

The term "computer" as used herein is a broad term, and is to be given its ordinary and customary meaning to a person of ordinary skill in the art (and it is not to be limited to a special or customized meaning), and refers without limitation to machine that can be programmed to manipulate data.

The terms "continuous analyte sensor," and "continuous glucose sensor," as used herein, are broad terms, and are to be given their ordinary and customary meaning to a person of ordinary skill in the art (and are not to be limited to a special or customized meaning), and refer without limitation to a device that continuously or continually measures a concentration of an analyte/glucose and/or calibrates the device (such as, for example, by continuously or continually adjusting or determining the sensor's sensitivity and background), for example, at time intervals ranging from fractions of a second up to, for example, 1, 2, or 5 minutes, or longer.

The phrase "continuous glucose sensing" as used herein is a broad term, and is to be given its ordinary and customary meaning to a person of ordinary skill in the art (and it is not to be limited to a special or customized meaning), and refers without limitation to the period in which monitoring of plasma glucose concentration is continuously or continually performed, for example, at time intervals ranging from fractions of a second up to, for example, 1, 2, or 5 minutes, or longer.

The term "counts," as used herein, is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "distal" as used herein is a broad term, and is to be given its ordinary and customary meaning to a person of ordinary skill in the art (and it is not to be limited to a special or customized meaning), and refers without limitation to spaces relatively far from a point of reference, such as an origin or a point of attachment.

The term "domain," as used herein, is a broad term, and is to be given its ordinary and customary meaning to a person of ordinary skill in the art (and is not to be limited to a special or customized meaning), and refers without limitation to regions of a membrane that can be layers, uniform or non-uniform gradients (for example, anisotropic), functional aspects of a material, or provided as portions of the membrane.

The term "electrical conductor," as used herein, is a broad term, and is to be given its ordinary and customary meaning to a person of ordinary skill in the art (and is not to be limited to a special or customized meaning) and refers without limitation to materials that contain movable charges of electricity. When an electric potential difference is impressed across separate points on a conductor, the mobile charges within the conductor are forced to move, and an electric current between those points appears in accordance with Ohm's law.

The term "electrical conductance," as used herein, is a broad term, and is to be given its ordinary and customary meaning to a person of ordinary skill in the art (and is not to be limited to a special or customized meaning) and refers without limitation to the propensity of a material to behave as an electrical conductor. In some embodiments, the term refers to a sufficient amount of electrical conductance (e.g., material property) to provide a necessary function (electrical conduction).

The terms "electrochemically reactive surface" and "electroactive surface," as used herein, are broad terms, and are to be given their ordinary and customary meaning to a person of ordinary skill in the art (and they are not to be limited to a special or customized meaning), and refer without limitation to the surface of an electrode where an electrochemical reaction takes place. In one embodiment, a working electrode measures hydrogen peroxide ($H_2O_2$) creating a measurable electronic current.

The term "electrode" as used herein is a broad term, and is to be given its ordinary and customary meaning to a person of ordinary skill in the art (and it is not to be limited to a special or customized meaning), and refers without limitation to a conductor through which electricity enters or leaves something such as a battery or a piece of electrical equipment. In one embodiment, the electrodes are the metallic portions of a sensor (e.g., electrochemically reactive surfaces) that are exposed to the extracellular milieu, for detecting the analyte. In some embodiments, the term electrode includes the conductive wires or traces that electrically connect the electrochemically reactive surface to connectors (for connecting the sensor to electronics) or to the electronics.

The term "enzyme" as used herein is a broad term, and is to be given its ordinary and customary meaning to a person of ordinary skill in the art (and it is not to be limited to a special or customized meaning), and refers without limitation to a protein or protein-based molecule that speeds up a chemical reaction occurring in a living thing. Enzymes may act as catalysts for a single reaction, converting a reactant (also called an analyte herein) into a specific product. In one embodiment of a glucose oxidase-based glucose sensor, an enzyme, glucose oxidase (GOX) is provided to react with glucose (the analyte) and oxygen to form hydrogen peroxide.

The term "filtering," as used herein, is a broad term, and is to be given its ordinary and customary meaning to a person of ordinary skill in the art (and is not to be limited to a special or customized meaning), and refers without limitation to modification of a set of data to make it smoother and more continuous and remove or diminish outlying points, for example, by performing a moving average of the raw data stream.

The term "function" as used herein is a broad term, and is to be given its ordinary and customary meaning to a person of ordinary skill in the art (and it is not to be limited to a special or customized meaning), and refers without limitation to an action or use for which something is suited or designed.

The term "GOx" as used herein is a broad term, and is to be given its ordinary and customary meaning to a person of ordinary skill in the art (and is not to be limited to a special or customized meaning), and refers without limitation to the enzyme Glucose Oxidase (e.g., GOx is an abbreviation).

The term "helix," as used herein, is a broad term, and is to be given its ordinary and customary meaning to a person of ordinary skill in the art (and is not to be limited to a special or customized meaning), and refers without limitation to a spiral or coil, or something in the form of a spiral or coil (such as, for example, a corkscrew or a coiled spring). In one example, a helix is a mathematical curve that lies on a cylinder or cone and makes a constant angle with the straight lines lying in the cylinder or cone. A "double helix" is a pair of parallel helices intertwined about a common axis, such as but not limited to that in the structure of DNA.

The term "host," as used herein, is a broad term, and is to be given its ordinary and customary meaning to a person of ordinary skill in the art (and is not to be limited to a special or customized meaning), and refers without limitation to animals, including humans.

The term "inactive enzyme," as used herein, is a broad term, and is to be given its ordinary and customary meaning to a person of ordinary skill in the art (and is not to be limited to a special or customized meaning), and refers without limitation to an enzyme (such as, for example, glucose oxidase, GOx) that has been rendered inactive (e.g., by denaturing of the enzyme) and has substantially no enzymatic activity. Enzymes can be inactivated using a variety of techniques known in the art, such as but not limited to heating, freeze-thaw, denaturing in organic solvent, acids or bases, cross-linking, genetically changing enzymatically critical amino acids, and the like. In some embodiments, a solution containing active enzyme can be applied to the sensor, and the applied enzyme subsequently inactivated by heating or treatment with an inactivating solvent.

The terms "insulative properties," "electrical insulator," and "insulator," as used herein, are broad terms, and are to be given their ordinary and customary meaning to a person of ordinary skill in the art (and are not to be limited to a special or customized meaning) and refer without limitation to the tendency of materials that lack mobile charges to prevent movement of electrical charges between two points. In one embodiment, an electrically insulative material may be placed between two electrically conductive materials, to prevent movement of electricity between the two electrically conductive materials. In some embodiments, the terms refer to a sufficient amount of insulative property (e.g., of a material) to provide a necessary function (electrical insulation). The terms "insulator" and "non-conductive material" can be used interchangeably herein.

The terms "interferent" and "interfering species," as used herein, are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured, producing a false positive signal.

The term "in vivo portion" as used herein is a broad term, and is to be given its ordinary and customary meaning to a person of ordinary skill in the art (and is not to be limited to a special or customized meaning), and refers without limitation to a portion of a device that is to be implanted or inserted into the host. In one embodiment, an in vivo portion of a transcutaneous sensor is a portion of the sensor that is inserted through the host's skin and resides within the host.

The term "membrane system," as used herein, is a broad term, and is to be given its ordinary and customary meaning to a person of ordinary skill in the art (and is not to be limited to a special or customized meaning), and refers without limitation to a permeable or semi-permeable membrane that can include two or more domains and is typically constructed of materials of a few microns thickness or more, which may be permeable to oxygen and are optionally permeable to glucose. In one example, the membrane system comprises an immobilized glucose oxidase enzyme, which enables an electrochemical reaction to occur to measure a concentration of glucose.

The term "operably connected," as used herein, is a broad term, and is to be given its ordinary and customary meaning to a person of ordinary skill in the art (and is not to be limited to a special or customized meaning), and refers without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "potentiostat," as used herein, is a broad term, and is to be given its ordinary and customary meaning to a person of ordinary skill in the art (and is not to be limited to a special or customized meaning), and refers without limitation to an electrical system that applies a potential between the working and reference electrodes of a two- or three-electrode cell at a preset value and measures the current flow through the working electrode. The potentiostat forces whatever current is necessary to flow between the working and counter electrodes to keep the desired potential, as long as the needed cell voltage and current do not exceed the compliance limits of the potentiostat.

The terms "processor module" and "microprocessor" as used herein are broad terms, and are to be given their ordinary and customary meaning to a person of ordinary skill in the art (and they are not to be limited to a special or customized meaning), and refer without limitation to a computer system, state machine, processor, or the like designed to perform arithmetic and logic operations using logic circuitry that responds to and processes the basic instructions that drive a computer.

The term "proximal" as used herein is a broad term, and is to be given its ordinary and customary meaning to a person of ordinary skill in the art (and it is not to be limited to a special or customized meaning), and refers without limitation to near to a point of reference such as an origin or a point of attachment.

The terms "raw data stream" and "data stream," as used herein, are broad terms, and are to be given their ordinary and customary meaning to a person of ordinary skill in the art (and they are not to be limited to a special or customized meaning), and refer without limitation to an analog or digital signal directly related to the analyte concentration measured by the analyte sensor. In one example, the raw data stream is digital data in counts converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "RAM," as used herein, is a broad term, and is to be given its ordinary and customary meaning to a person of ordinary skill in the art (and is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "ROM," as used herein, is a broad term, and is to be given its ordinary and customary meaning to a person of ordinary skill in the art (and is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The terms "reference analyte values" and "reference data," as used herein, are broad terms, and are to be given their ordinary and customary meaning to a person of ordinary skill in the art (and they are not to be limited to a special or customized meaning), and refer without limitation to reference data from a reference analyte monitor, such as a blood glucose meter, or the like, including one or more reference data points. In some embodiments, the reference glucose values are obtained from a self-monitored blood glucose (SMBG) test (for example, from a finger or forearm blood test) or a YSI (Yellow Springs Instruments) test, for example.

The term "regression" as used herein is a broad term, and is to be given its ordinary and customary meaning to a person of ordinary skill in the art (and it is not to be limited to a special or customized meaning), and refers without limitation to finding a line in which a set of data has a minimal measurement (for example, deviation) from that line. Regression can be linear, non-linear, first order, second order, and so forth. One example of regression is least squares regression.

The term "sensing region," as used herein, is a broad term, and is to be given its ordinary and customary meaning to a person of ordinary skill in the art (and is not to be limited to a special or customized meaning), and refers without limitation to the region of a monitoring device responsible for the detection of a particular analyte. In one embodiment, the sensing region generally comprises a non-conductive body, at least one electrode, a reference electrode and a optionally a counter electrode passing through and secured within the body forming an electroactive surface at one location on the body and an electronic connection at another location on the body, and a membrane system affixed to the body and covering the electroactive surface.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (such as, for example, $H_2O_2$) associated with the measured analyte (such as, for example, glucose). For example, in one embodiment, a sensor has a sensitivity of from about 1 to about 300 picoAmps of current for every 1 mg/dL of glucose analyte.

The term "sensitivity profile" or "sensitivity curve," as used herein, are broad terms, and are to be given their ordinary and customary meaning to a person of ordinary skill in the art (and is not to be limited to a special or customized meaning), and refer without limitation to a representation of a change in sensitivity over time.

The terms "sensor analyte values" and "sensor data," as used herein, are broad terms, and are to be given their ordinary and customary meaning to a person of ordinary skill in the art (and they are not to be limited to a special or customized meaning), and refer without limitation to data received from a continuous analyte sensor, including one or more time-spaced sensor data points.

The terms "sensor electronics" and "electronic circuitry," as used herein, are broad terms, and are to be given their ordinary and customary meaning to a person of ordinary skill in the art (and they are not to be limited to a special or customized meaning), and refer without limitation to the components (for example, hardware and/or software) of a device configured to process data, e.g., a processor or processor electronics. In the case of an analyte sensor, the data includes biological information obtained by a sensor regarding the concentration of the analyte in a biological fluid. U.S. Pat. Nos. 4,757,022, 5,497,772 and 4,787,398 describe suitable electronic circuits that can be utilized with devices of certain embodiments.

The term "sensor environment," as used herein, is a broad term and is to be given its ordinary and customary meaning to a person of ordinary skill in the art (and is not to me limited to a special or customized meaning), and refers without limitation to the biological environment in which a sensor is operating.

The terms "substantial" and "substantially," as used herein, are broad terms, and are to be given their ordinary and customary meaning to a person of ordinary skill in the art (and are not to be limited to a special or customized meaning), and refer without limitation to being largely but not necessarily wholly that which is specified.

The term "thermal conductivity," as used herein is a broad term, and is to be given its ordinary and customary meaning to a person of ordinary skill in the art (and it is not to be limited to a special or customized meaning), and refers without limitation to the quantity of heat transmitted, due to unit temperature gradient, in unit time under steady conditions in a direction normal to a surface of unit area.

The term "thermal coefficient," as used herein is a broad term, and is to be given its ordinary and customary meaning to a person of ordinary skill in the art (and is not to be limited to a special or customized meaning), and refers without limitation to the change in resistance of a material at various temperatures.

The term "thermally conductive material," as used herein is a broad term, and is to be given its ordinary and customary meaning to a person of ordinary skill in the art (and is not to be limited to a special or customized meaning), and refers without limitation to materials displaying a high degree of thermal conductivity.

The term "twisted," as used herein, is a broad term, and is to be given its ordinary and customary meaning to a person of ordinary skill in the art (and it is not to be limited to a special or customized meaning), and refers without limitation to united by having one part or end turned in the opposite direction to the other, such as, but not limited to the twisted strands of fiber in a string, yarn, or cable.

Overview

Devices, systems, and methods for measuring, identifying, and responding to physiological conditions in tissue surrounding an implantable analyte sensor are provided. Conventional continuous analyte sensors lack the capability to measure various in vivo properties, and to identify and/or respond to changing physiological conditions surrounding the sensor.

Measuring in vivo properties and identifying a physiological response or condition allows the patient and physician to understand the host's reaction to the implantable sensor, and also enables the system or user to take appropriate steps in response to the identified condition. Certain measurements and identification steps can distinguish an actual decrease in glucose from a physiological response affecting the glucose sensor, for example. Additionally, the implantable sensor or system can be programmed to respond in a particular way to the identified condition. For example, as further discussed below, if a dip and recover condition is identified, the device may instruct the user that the sensor is temporarily out of service and that the appropriate response is to wait a certain number of hours until the condition resolves.

FIG. 1 illustrates a method according to one embodiment. After implantation of the sensor, a physiological response may occur at some time after implantation. In this illustrated embodiment, a sensor can be used to measure one or more properties of biological tissues surrounding the implant at 100. The one or more measured parameters are processed at step 102. Such measurements are subsequently used to identify a physiological condition or response of the body or a sensor failure at 104. In some embodiments, a quality score can be determined at 106. Finally, a proper response to the particular condition or quality score can be determined at 108. In addition to novel methods, devices and systems are also part of the preferred embodiments, and are discussed further below in more detail.

Measuring an In Vivo Property Generally

There are many devices, systems, and methods for measuring physiological conditions in tissue. Described herein are improved analyte sensors and related systems for measuring in vivo properties and conditions surrounding the sensors. Various arrangements for the sensor elements and related systems are contemplated. In some embodiments, the measuring device or system can be separate from the implantable analyte sensor. In some embodiments, the measuring device or system can be in communication with the sensor and/or in communication with a user interface. Yet in other embodiments, it may be preferable for the measuring device to be coupled to or integrated with the analyte sensor, or for the sensor itself to be configured to measure in vivo properties or physiological conditions in surrounding tissue.

Generally, implantable sensors measure a signal (e.g., counts) related to an analyte of interest in a host. For example, an electrochemical sensor can measure glucose, creatinine, or urea in a host, such as an animal, especially a human. Generally, the signal can be converted mathematically to a numeric value indicative of analyte status, such as analyte concentration. In some embodiments, the analyte sensor can be an invasive, minimally invasive, or non-invasive device, for example a subcutaneous, transdermal, or intravascular device. In some embodiments, the analyte sensor may analyze a plurality of intermittent biological samples. The analyte sensor may use any method of analyte-measurement, including enzymatic, chemical, physical, electrochemical, spectrophotometric, polarimetric, calorimetric, radiometric, or the like.

In general, analyte sensors provide at least one working electrode and at least one reference electrode, which are configured to measure a signal associated with a concentration of the analyte in the host, such as described in more detail below, and as appreciated by one skilled in the art.

Figure 8A:
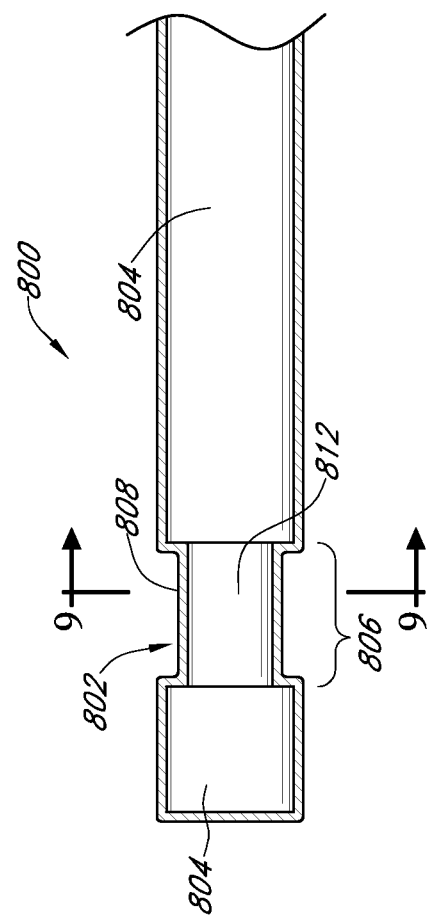
FIG. 8A is a side-view schematic illustrating an in vivo portion of an analyte sensor, in one embodiment.
Figure 8C:
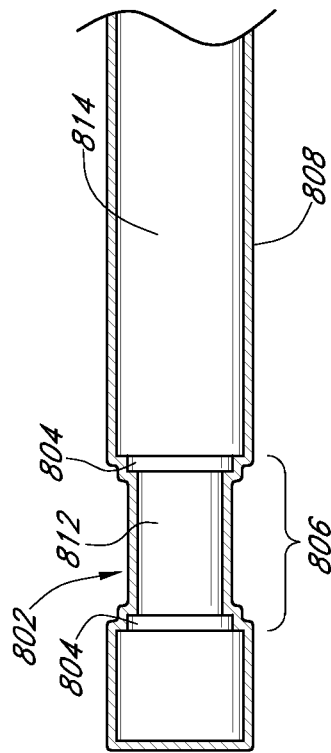
FIG. 8C is a side-view schematic illustrating an in vivo portion of an analyte sensor, in another embodiment.
Figure 8B:
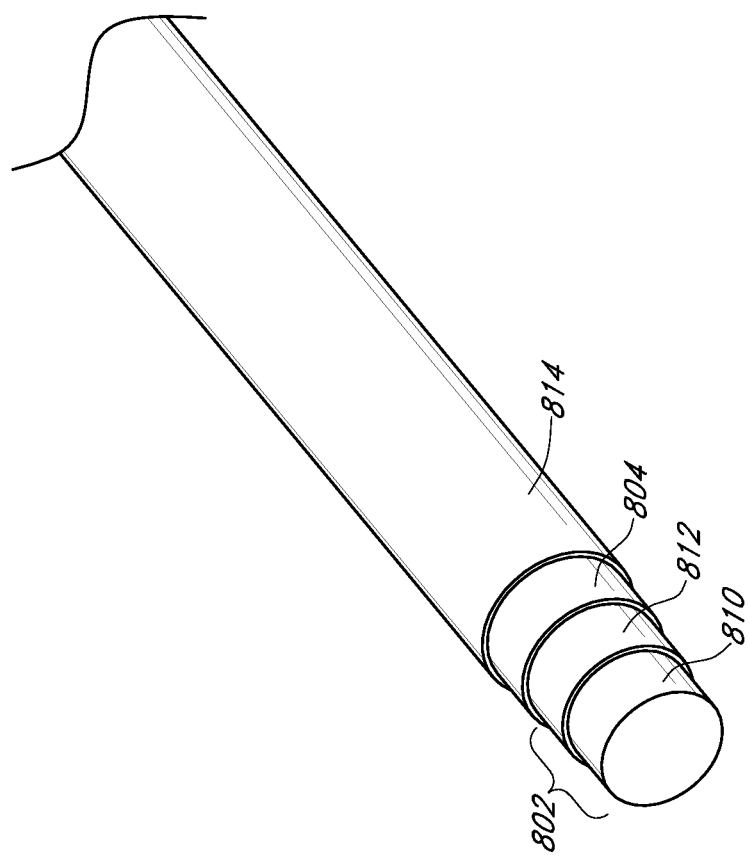
FIG. 8B is a perspective-view schematic illustrating an in vivo portion of an analyte sensor, in one embodiment.

FIGS. 8A-8C illustrate one exemplary embodiment of a single working electrode continuous analyte sensor 800. The sensor 800 comprises an elongated conductive body 802, which includes a core 810 (see FIG. 8B) and a first layer 812 at least partially surrounding the core. The first layer includes a working electrode (e.g., located in window 806) and a membrane 808 located over the working electrode configured and arranged for multi-axis bending. In some embodiments, the core and first layer can be of a single material (e.g., platinum). In some embodiments, the elongated conductive body is a composite of at least two materials, such as a composite of two conductive materials, or a composite of at least one conductive material and at least one non-conductive material. In some embodiments, the elongated conductive body comprises a plurality of layers. In certain embodiments, there are at least two concentric (e.g., annular) layers, such as a core formed of a first material and a first layer formed of a second material. However, additional layers can be included in some embodiments. In some embodiments, the layers are coaxial.

The elongated conductive body may be long and thin, yet flexible and strong. For example, in some embodiments, the smallest dimension of the elongated conductive body is less than about 0.1 inches, 0.075 inches, 0.05 inches, 0.025 inches, 0.01 inches, 0.004 inches, or 0.002 inches. While the elongated conductive body is illustrated in FIGS. 8A-8C as having a circular or substantially circular cross-section, in other embodiments the cross-section of the elongated conductive body can be ovoid, rectangular, triangular, polyhedral, star-shaped, C-shaped, T-shaped, X-shaped, Y-Shaped, irregular, or the like. In one embodiment, a conductive wire electrode is employed as a core. To such a clad electrode, two additional conducting layers may be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

In addition to providing structural support, resiliency and flexibility, in some embodiments, the core 810 (or a component thereof) provides electrical conduction for an electrical signal from the working electrode to sensor electronics (not shown), which are described elsewhere herein. In some embodiments, the core 810 comprises a conductive material, such as titanium, stainless steel, tantalum, a conductive polymer, and/or the like. However, in other embodiments, the core is formed from a non-conductive material, such as a non-conductive polymer. In yet other embodiments, the core comprises a plurality of layers of materials. For example, in one embodiment the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is conductive material selected to provide electrical conduction between the core and the first layer, and/or to attach the first layer to the core (e.g., if the first layer is formed of a material that does not attach well to the core material). In another embodiment, the core is formed of a non-conductive material (e.g., a non-conductive metal and/or a non-conductive polymer) and the first layer is a conductive material, such as titanium, stainless steel, tantalum, a conductive polymer, and/or the like. The core and the first layer can be of a single (or same) material, e.g., platinum. One skilled in the art appreciates that additional configurations are possible.

Referring again to FIGS. 8A-8C, in some embodiments, the first layer 812 is formed of a conductive material. The working electrode is an exposed portion of the surface of the first layer. Accordingly, the first layer is formed of a material configured to provide a suitable electroactive surface for the working electrode, a material such as but not limited to platinum, platinum-iridium, gold, palladium, iridium, graphite, carbon, a conductive polymer, an alloy and/or the like.

As illustrated in FIGS. 8B-8C, a second layer 804 surrounds a least a portion of the first layer 812, thereby defining the boundaries of the working electrode. In some embodiments, the second layer 804 serves as an insulator and is formed of an insulating material, such as polyimide, polyurethane, parylene, or any other known insulating materials. For example, in one embodiment the second layer is disposed on the first layer and configured such that the working electrode is exposed via window 806. In another embodiment, an elongated conductive body, including the core, the first layer and the second layer, is provided, and the working electrode is exposed (i.e., formed) by removing a portion of the second layer, thereby forming the window 806 through which the electroactive surface of the working electrode (e.g., the exposed surface of the first layer) is exposed. In some embodiments, the working electrode is exposed by (e.g., window 806 is formed by) removing a portion of the second and (optionally) third layers. Removal of coating materials from one or more layers of elongated conductive body (e.g., to expose the electroactive surface of the working electrode) can be performed by hand, excimer lasing, chemical etching, laser ablation, grit-blasting, or the like.

In some embodiments, the sensor further comprises a third layer 814 comprising a conductive material. In further embodiments, the third layer may comprise a reference electrode, which may be formed of a silver-containing material that is applied onto the second layer (e.g., an insulator). The silver-containing material may include any of a variety of materials and be in various forms, such as, Ag/AgCl-polymer pastes, paints, polymer-based conducting mixture, and/or inks that are commercially available, for example. The third layer can be processed using a pasting/dipping/coating step, for example, using a die-metered dip coating process. In one exemplary embodiment, an Ag/AgCl polymer paste is applied to an elongated body by dip-coating the body (e.g., using a meniscus coating technique) and then drawing the body through a die to meter the coating to a precise thickness. In some embodiments, multiple coating steps are used to build up the coating to a predetermined thickness. Such a drawing method can be utilized for forming one or more of the electrodes in the device depicted in FIG. 8B.

In some embodiments, the silver grain in the Ag/AgCl solution or paste can have an average particle size corresponding to a maximum particle dimension that is less than about 100 microns, or less than about 50 microns, or less than about 30 microns, or less than about 20 microns, or less than about 10 microns, or less than about 5 microns. The silver chloride grain in the Ag/AgCl solution or paste can have an average particle size corresponding to a maximum particle dimension that is less than about 100 microns, or less than about 80 microns, or less than about 60 microns, or less than about 50 microns, or less than about 20 microns, or less than about 10 microns. The silver grain and the silver chloride grain may be incorporated at a ratio of the silver chloride grain:silver grain of from about 0.01:1 to 2:1 by weight, or from about 0.1:1 to 1:1. The silver grains and the silver chloride grains are then mixed with a carrier (e.g., a polyurethane) to form a solution or paste. In certain embodiments, the Ag/AgCl component form from about 10% to about 65% by weight of the total Ag/AgCl solution or paste, or from about 20% to about 50%, or from about 23% to about 37%. In some embodiments, the Ag/AgCl solution or paste has a viscosity (under ambient conditions) that is from about 1 to about 500 centipoise, or from about 10 to about 300 centipoise, of from about 50 to about 150 centipoise.

In some embodiments, the elongated conductive body further comprises one or more intermediate layers located between the core and the first layer. For example, in some embodiments, the intermediate layer is an insulator, a conductor, a polymer, and/or an adhesive.

In certain embodiment, the core comprises a non-conductive polymer and the first layer comprises a conductive material. Such a sensor configuration can sometimes provide reduced material costs, in that it replaces a typically expensive material with an inexpensive material. For example, in some embodiments, the core is formed of a non-conductive polymer, such as, a nylon or polyester filament, string or cord, which can be coated and/or plated with a conductive material, such as platinum, platinum-iridium, gold, palladium, iridium, graphite, carbon, a conductive polymer, and allows or combinations thereof.

As illustrated in FIG. 8C, the sensor also includes a membrane 808 covering at least a portion of the working electrode. Membranes are discussed in detail in greater detail elsewhere herein, for example, with reference to FIGS. 9A-9C.

In embodiments wherein an outer insulator is disposed, a portion of the coated assembly structure can be stripped or otherwise removed, for example, by hand, excimer lasing, chemical etching, laser ablation, grit-blasting, or the like, to expose the electroactive surfaces. Alternatively, a portion of the electrode can be masked prior to depositing the insulator in order to maintain an exposed electroactive surface area.

In some embodiments, a radial window is formed through the insulating material to expose a circumferential electroactive surface of the working electrode. Additionally, sections of electroactive surface of the reference electrode are exposed. For example, the sections of electroactive surface can be masked during deposition of an outer insulating layer or etched after deposition of an outer insulating layer. In some applications, cellular attack or migration of cells to the sensor can cause reduced sensitivity or function of the device, particularly after the first day of implantation. However, when the exposed electroactive surface is distributed circumferentially about the sensor (e.g. as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

In some embodiments, a single working electrode sensor can be configured to measure and detect various in vivo properties and physiological changes and conditions. Such types of electrode and sensor can, for example, be coupled with or integrated with or in communication with devices or systems that measure and detect various in vivo properties and physiological conditions. In one embodiment, a single-working-electrode-based sensor system is capable of measuring both an analyte concentration and physiological changes/conditions in a sensor environment through bias potential. When powered at its normal bias potential, the single working electrode is in a mode for analyte concentration (e.g., glucose concentration) measurement. With this embodiment, at certain times, the bias potential may be changed. For example, the bias potential may be decreased to a level such that the working electrode can no longer oxidize the measured species (e.g., hydrogen peroxide) that is indicative of glucose concentration. Nonetheless, at a lower bias potential, the working electrode may be capable of measuring some other parameter that is indicative of physiological conditions or changes. With this embodiment, the working electrode's bias potential may alternate from one bias potential (e.g., for measuring glucose) to another bias potential (for measuring another parameter, such as a parameter related to sensor environment). The timing and frequency of the changes in applied bias potential may be dependent on certain parameters that are indicative of a possible change involving the sensor environment. For example, if the system detects a high rate of temperature change, the system may be configured to apply the bias potential used to measure temperature change. In another embodiment, as described elsewhere herein in greater detail, the bias potential may be altered to measure oxygen concentration and oxygen concentration changes, which may be indicative of certain physiological changes to the sensor environment (e.g., encapsulation of the sensor).

Figure 9A:
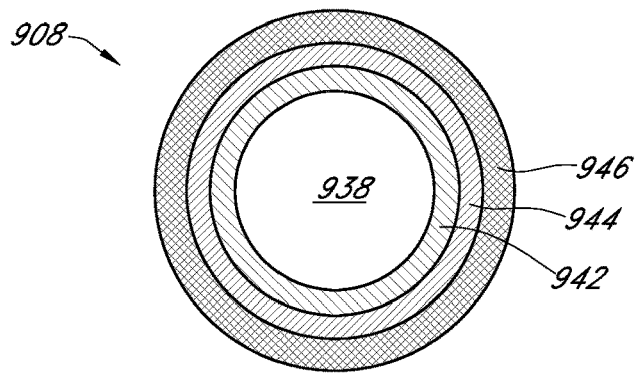
FIGS. 9A-9C are cross-sectional views through the sensor of FIG. 8A on line 9-9, illustrating various embodiments of the membrane system.

FIG. 9A is a cross-sectional view through the sensor of FIG. 8A on line 9-9, illustrating one embodiment of the membrane system 908. In this particular embodiment, the membrane system includes an interference domain 942, an enzyme domain 944, and a diffusion resistance domain 946 located around the working electrode 938, all of which are described in more detail elsewhere herein.

Figure 9B:
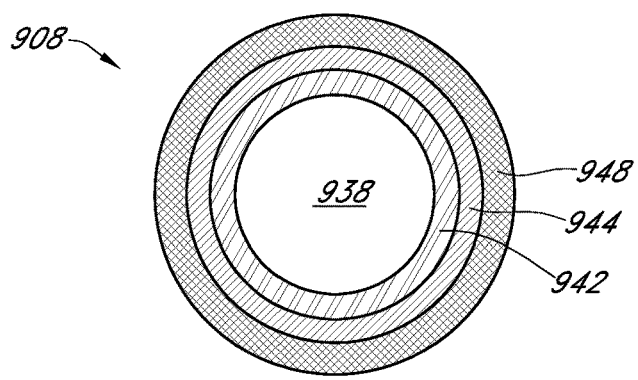

As illustrated in FIG. 9B, in some embodiments, the membrane system may include a bioprotective domain 948, also referred to as a cell-impermeable domain or biointerface domain, comprising a surface-modified base polymer as described in more detail elsewhere herein. In some embodiments, a unitary diffusion resistance domain and bioprotective domain may be included in the membrane system (e.g., wherein the functionality of both domains is incorporated into one domain, i.e., the bioprotective domain). In some embodiments, the sensor is configured for short-term implantation (e.g., from about 1 to 30 days). However, it is understood that the membrane system 908 can be modified for use in other devices, for example, by including only one or more of the domains, or additional domains.

Figure 9C:
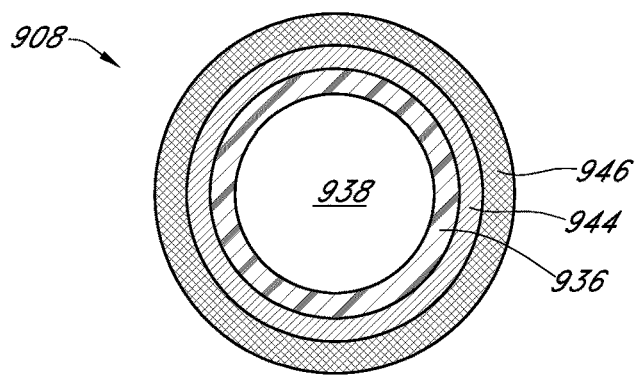

As illustrated in FIG. 9C, in some embodiments, the membrane system may include an electrode domain 936. The electrode domain 936 is provided to ensure that an electrochemical reaction occurs between the electroactive surfaces of the working electrode and the reference electrode, and thus the electrode domain may be situated more proximal to the electroactive surfaces than the interference and/or enzyme domain. The electrode domain may include a coating that maintains a layer of water at the electrochemically reactive surfaces of the sensor. In other words, the electrode domain may be present to provide an environment between the surfaces of the working electrode and the reference electrode, which facilitates an electrochemical reaction between the electrodes.

A wide variety of configurations and combinations for the various layers in the membrane system are encompassed by the preferred embodiments. In various embodiments, any of the domains illustrated in FIGS. 9A-9C may be omitted, altered, substituted for, and/or incorporated together without departing from the spirit of the preferred embodiments. It is to be understood that sensing membranes modified for other sensors, for example, may include fewer or additional layers. For example, in some embodiments, the membrane system may comprise one electrode layer, one enzyme layer, and two bioprotective layers, but in other embodiments, the membrane system may comprise one electrode layer, two enzyme layers, and one bioprotective layer. In some embodiments, the bioprotective layer may be configured to function as the diffusion resistance domain and control the flux of the analyte (e.g., glucose) to the underlying membrane layers.

In some embodiments, one or more domains of the sensing membranes may be formed from materials such as polytetrafluoroethylene, silicone, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some embodiments, the sensing membrane can be deposited on the electroactive surfaces of the electrode material using known thin or thick film techniques (for example, spraying, electro-depositing, dipping, or the like). It should be appreciated that the sensing membrane located over the working electrode does not have to have the same structure as the sensing membrane located over the reference electrode; for example, the enzyme domain deposited over the working electrode does not necessarily need to be deposited over the reference or counter electrodes.

Although the exemplary embodiments illustrated in FIGS. 9A-9C involve circumferentially extending membrane systems, the membranes described herein may be applied to any planar or non-planar surface, for example, the substrate-based sensor structure of U.S. Pat. No. 6,565,509 to Say et al.

It is to be understood that the different embodiments of the membrane/membrane system described above can be applied to any of the sensors/sensor systems described herein. Additionally, it is also to be understood that any of the membranes (including membrane layers and domains), membrane properties, and membrane-derived results disclosed in the following publications and application can be used with any of the sensors/sensor systems described herein: U.S. Patent Application Publication No. 2009/0247856 A1, U.S. Patent Application Publication No. 2010/020341 A1, and U.S. Patent Application Publication No. 2013/0053665 A1, and U.S. patent application Ser. No. 13/779,607, and U.S. patent application Ser. No. 13/836,530 entitled "Membranes for Continuous Analyte Sensors" and filed on Mar. 15, 2013, which are incorporated by reference herein in their entirety.

In certain embodiments, the sensor comprises at least two working electrodes (in some embodiments, one with and one without enzyme over its electroactive surface), and sensor electronics operably connected to the working and auxiliary electrodes. The analyte sensors can also comprise at least one additional working electrode configured to measure at least one additional signal. For example, in some embodiments, the additional signal can be associated with the baseline and/or sensitivity of the analyte sensor, thereby enabling monitoring of baseline and/or sensitivity changes that may occur in a continuous analyte sensor over time. Preferably, each electrode can be formed from a fine wire, with a diameter in the range of 0.001 to 0.01 inches, for example, and may be formed from plated wire or bulk material, however the electrodes may be deposited on a substrate or other known configurations as is appreciated by one skilled in the art. In some embodiments, such electrodes and sensors can be configured to measure and detect various in vivo properties and physiological changes and conditions. Such electrodes and sensors can also be coupled with or integrated with or in communication with devices or systems that measure and detect various in vivo properties and physiological conditions.

Figure 2:
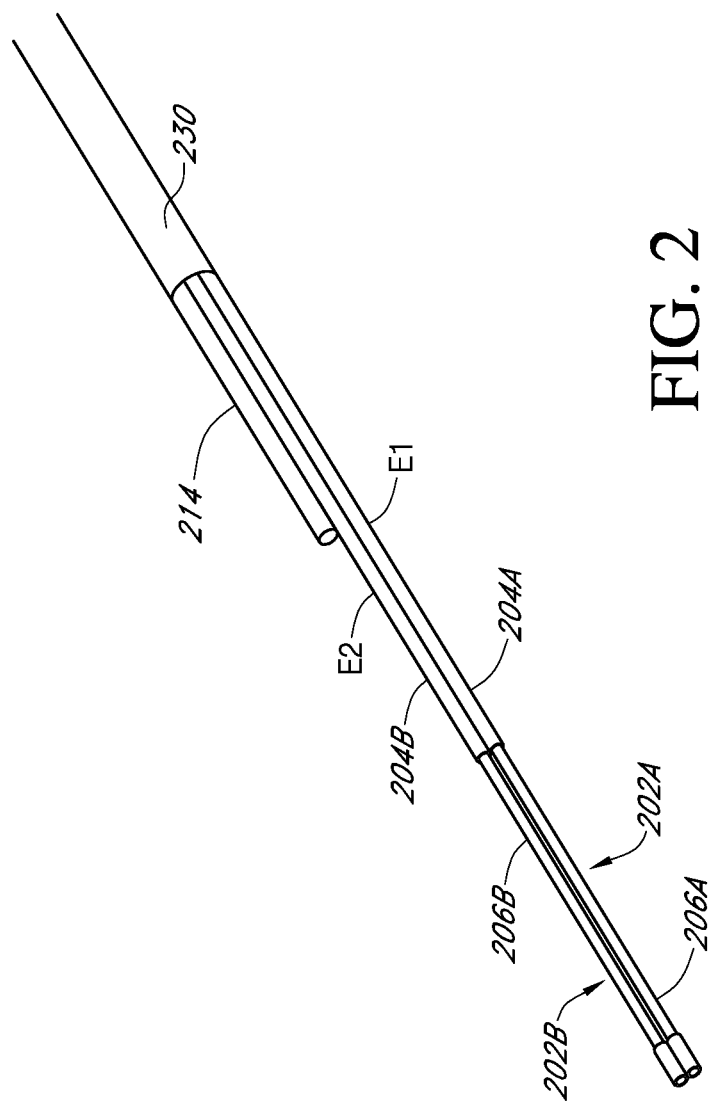
FIG. 2 is a perspective-view schematic illustrating an in vivo portion of a multi-electrode analyte sensor, in one embodiment.

FIG. 2 schematically illustrates the in vivo portion of one embodiment of a dual-electrode analyte sensor. For example, the sensor can comprise first and second elongated bodies (such as, for example, conductive cores) E1, E2. Further, a working electrode can comprise an exposed electroactive surface of the elongated body and a reference electrode 214. The reference electrode can be bundled together with the first and second elongated bodies E1, E2, for example. Moreover, each working electrode can comprise a conductive core. For example, the first working electrode can comprise an exposed portion of the surface of a first elongated body 202A having an insulating material 204A disposed thereon, such that the portion of the surface of the elongated body (that is, the working electrode) is exposed via a radial window 206A in the insulator. The insulating material 204A can comprise a polymer, such as, a non-conductive (that is, dielectric) polymer. The insulating material can include, for example, at least one of polyurethane, polyimide or parylene.

The elongated body may comprise a core and a first layer, wherein an exposed (that is, electroactive) surface of the first layer is the first working electrode. The second working electrode can comprise an exposed surface of a second elongated body 202B having an insulator 204B disposed thereon, such that a portion of the surface of the elongated body is exposed via a radial window 206B in the insulator. A first layer (not shown) can be applied to the exposed surface of the second core to form the second working electrode. Accordingly, the radial windows can be spaced such that the working electrodes (that is, the electroactive surfaces) are substantially overlapping along the length of the sensor. However, in other embodiments, the working electrodes can be spaced such that they are not substantially overlapping along the length of the sensor. The reference electrode can comprise a wire (such as, for example, Ag/AgCl wire) wrapped around the bundled conductive cores. Alternatively, the reference electrode can comprise a layer of silver-containing material applied to at least one of the conductive cores.

As further shown in FIG. 2, one or more connectors can be configured and arranged to hold the conductive cores and reference electrode together. For example, a tube 230 or heat shrink material can be employed as a connector and/or supporting member. The tubing or heat shrink material may include an adhesive inside the tube so as to provide enhanced adhesion to the components secured within (such as, for example, wire(s), core, layer materials, etc.). In such a configuration, the heat-shrink material functions not only as an insulator, but also to hold the proximal ends of the sensor together so as to prevent or reduce fatigue and/or to maintain the electrodes together in the event of a fatigue failure. The wires need not be a core and a layer, but can instead comprise bulk materials.

The distal ends of the sensor can be loose and finger-like, as depicted in FIG. 2, for example. Alternatively, the distal ends of the sensor can be held together with an end cap. A reference electrode can be placed on one or more of the first and second elongated bodies instead of being provided as a separate electrode, and the first and second elongated bodies including at least one reference electrode thereof can be bundled together. Heat shrink tubing, crimp wrapping, dipping, or the like can be employed to bundle one or more elongated bodies together. In some embodiments, the reference electrode is a wire, such as described elsewhere herein. In other embodiments, the reference electrode comprises a foil. In an embodiment of a dual-electrode analyte sensor, the first and second elongated bodies can be present as or formed into a twisted pair, which is subsequently bundled with a wire or foil reference electrode. Connectors, which can also function as supporting members, can be configured and arranged to hold the conductive cores and reference electrode together.

Figure 3C:
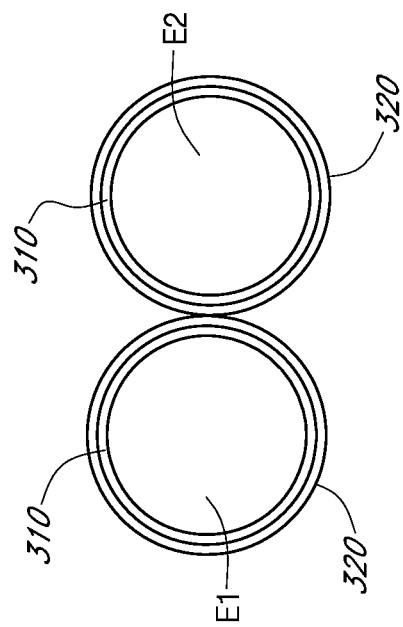
FIG. 3C is a front view of the sensor embodiment illustrated in FIGS. 3A and 3B.
Figure 3B:
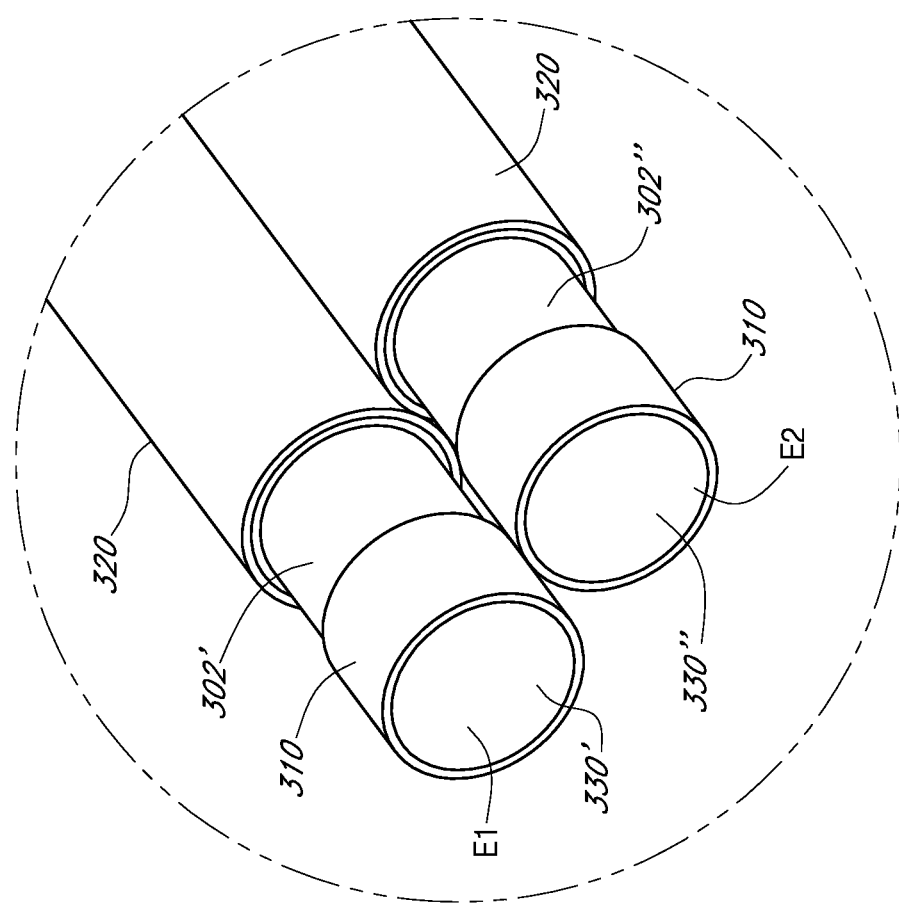
FIG. 3B is a close perspective schematic of the distal portion of the sensor embodiment illustrated in FIG. 3A.

FIG. 3A is a perspective view of the in vivo portion of one embodiment of a multi-electrode sensor system 300. The electrode system 300 may comprise two working electrodes and at least one reference/counter electrode. The sensor system 300 comprises first and second elongated bodies E1, E2. The first and second elongated bodies E1, E2 each can be formed of a conductive core. Alternatively, the first and second elongated bodies E1, E2 can be formed of a core with a conductive layer deposited thereon. As shown in FIG. 3A, for example, an insulating layer 310, a conductive layer 320, and a membrane layer (not shown) can be deposited on top of the first and second elongated bodies E1, E2. The insulating layer 310 can separate the conductive layer 320 from the elongated body. The materials selected to form the insulating layer 310 may include any of the insulating materials described elsewhere herein. For example, the insulating layer can comprise a non-conductive polymer, such as, polyurethane or polyimide. The materials selected to form the conductive layer 320 may include, for example, platinum, platinum-iridium, gold, palladium, iridium, graphite, silver/silver chloride, carbon, a conductive polymer, an alloy, and the like. Working electrodes 302', 302" can be formed by removing a portion of the conductive layer 320 and the insulating layer 310, thereby exposing an electroactive surface of the first and second elongated bodies E1, E2. FIG. 3B provides a close perspective view of the distal portion of the elongated bodies E1, E2. FIG. 3C provides a front view of the sensor illustrated in FIGS. 3A and 3B.

The two elongated bodies illustrated in FIG. 3A can be fabricated to have substantially the same shape and dimensions. The working electrodes can be fabricated to have the same properties, thereby providing a sensor system capable of providing redundancy of signal measurements. In other embodiments, the working electrodes, associated with the elongated bodies E1, E2, may each have one or more characteristics that distinguish each working electrode from the other. For example, in one embodiment, each of the elongated bodies E1, E2 may be covered with a different membrane, so that each working electrode has a different membrane property than the other working electrode. For example, one of the working electrodes may have a membrane comprising an enzyme layer and the other working electrode may have a membrane comprising a layer having either an inactivated form of the enzyme or no enzyme.

Although not shown in FIGS. 3A-3C, the distal ends 330', 330" of the core portions of the elongated bodies E1, E2, respectively, can be covered with an insulating material (such as, for example, polyurethane or polyimide). Alternatively, the exposed core portions 330', 330" can be covered with a membrane system and serve as an additional working electrode surface area.

Figure 4C:
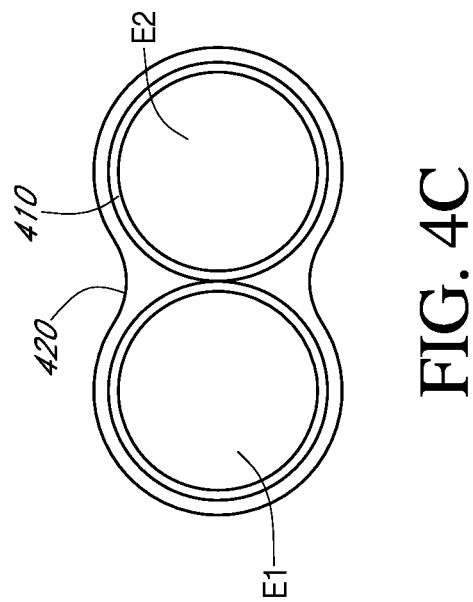
FIG. 4C is a front view of the sensor embodiment illustrated in FIGS. 4A and 4B.
Figure 4B:
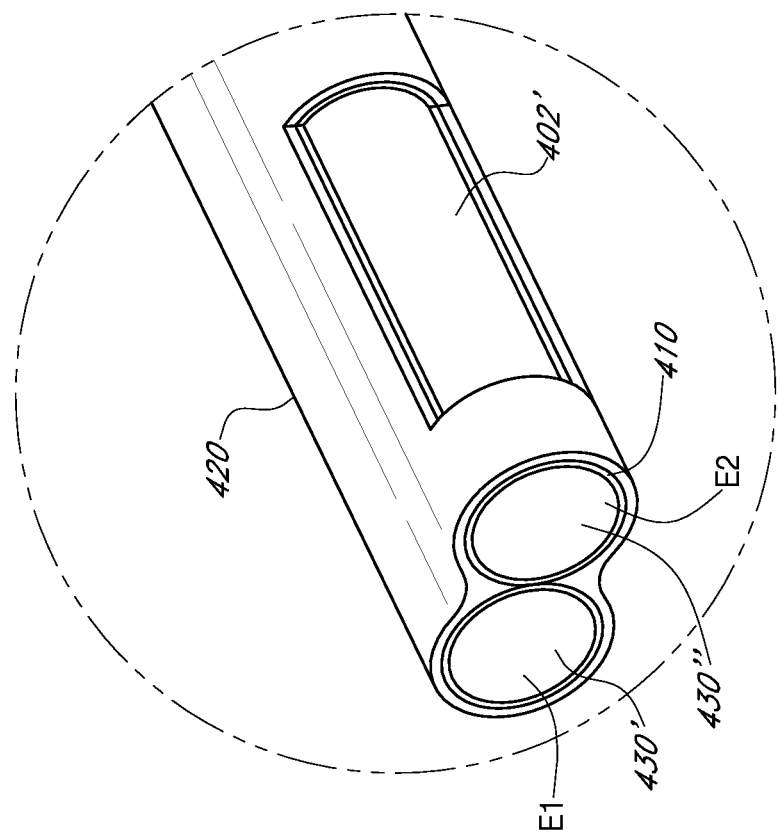
FIG. 4B is a close perspective schematic of the distal portion of the sensor embodiment illustrated in FIG. 4A.

FIG. 4A is a perspective view of the in vivo portion of an embodiment of a multi-electrode sensor system 400 comprising two working electrodes and at least one reference/counter electrode. The sensor system 400 comprises first and second elongated bodies E1, E2. First and second elongated bodies, E1, E2 each can be formed of a conductive core. Alternatively, first and second elongated bodies E1, E2 can be formed of a core with a conductive layer deposited thereon. An insulating layer 410 can be deposited onto each elongated body E1, E2. Furthermore, a conductive domain 420 and a membrane layer (not shown) can be deposited on top of an assembly comprising the elongated bodies E1, E2 and the insulating layer 410. The conductive domain 420 can bind the two elongated bodies E1, E2 into one elongated body. The insulating layers 410 surrounding each elongated body E1, E2 can prevent electrical contact between the two elongated bodies E1, E2. The materials selected to form the insulating layer 410 can include any of the insulating materials described elsewhere herein, including, for example, polyurethane and polyimide. The materials selected to form the conductive domain 420 can include any of the conductive materials described elsewhere herein, including, for example silver/silver-chloride and platinum. Working electrode 402' on elongated body E1 and another working electrode (not shown) on elongated body E2, can be formed by removing a portion of the conductive domain 420 and a portion of the insulating layer 410, thereby exposing electroactive surfaces of elongated bodies E1, E2. The portion of the conductive domain 420 not removed can form the reference/counter electrode. FIG. 4B provides a close perspective view of the distal portion of the elongated bodies E1, E2. FIG. 4C provides a front view of the sensor embodiment illustrated in FIGS. 4A and 4B.

In some embodiments, it may be preferable to have a multi-working-electrode sensor that shares a common electrical connection, i.e., a sensor comprising multiple working electrodes that share a common connection (e.g., electrical connection). It has been found that certain biological responses to an implantable device can often be very localized. Accordingly, challenges may arise involving biological events that are localized to a specific region and that interfere with the performance of a sensor. If that specific region is near a single working electrode, and that sensor only has that single working electrode for measuring glucose, then measurements may be inaccurate. To overcome this, in some embodiments, sensors are designed with single or a plurality of electrodes, with each electrode comprising a plurality of working electrodes (e.g., exposed through windows).

Figure 12:
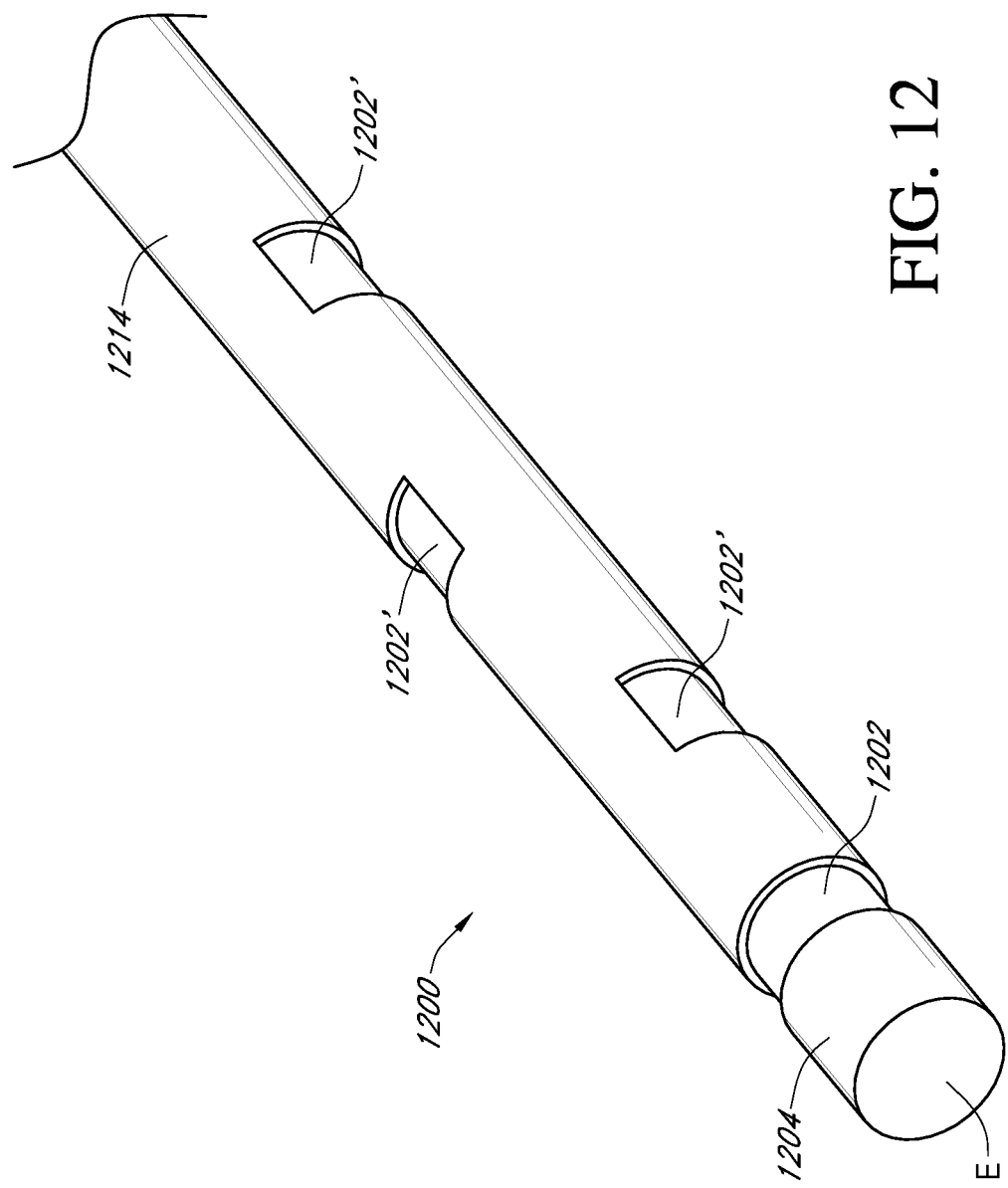
FIG. 12 is a perspective-view schematic illustrating an in vivo portion of a single-electrode analyte sensor, with the electrode comprising a plurality of working electrodes exposed through windows.

FIG. 12 is a perspective-view schematic illustrating an in vivo portion of a single-working-electrode analyte sensor 1200, wherein the elongated body E comprises a plurality of working electrodes 1202, 1202' exposed through windows. In this embodiment, window 1202 can be formed by completely removing (360 degrees around the perimeter of the elongated body) a portion of a conductive layer 1214 and an insulating layer 1204, thereby exposing an electroactive surface of the window 1202. Windows 1202' can be formed by removing a cut portion (i.e., a cut that does not correspond to 360 degrees around the perimeter of the elongated body) of the conductive layer 1214 and a portion of the insulating layer 1204, thereby exposing electroactive surfaces of elongated body E. All the working electrodes 1202' and 1202 share a common electrical connection. In certain embodiments, the conductive layer 1214 may function as a reference electrode and may be formed of any of a variety of materials and be in various forms, such as, Ag/AgCl-polymer pastes, paints, polymer-based conducting mixture, and/or inks that are commercially available, for example.

Figure 13:
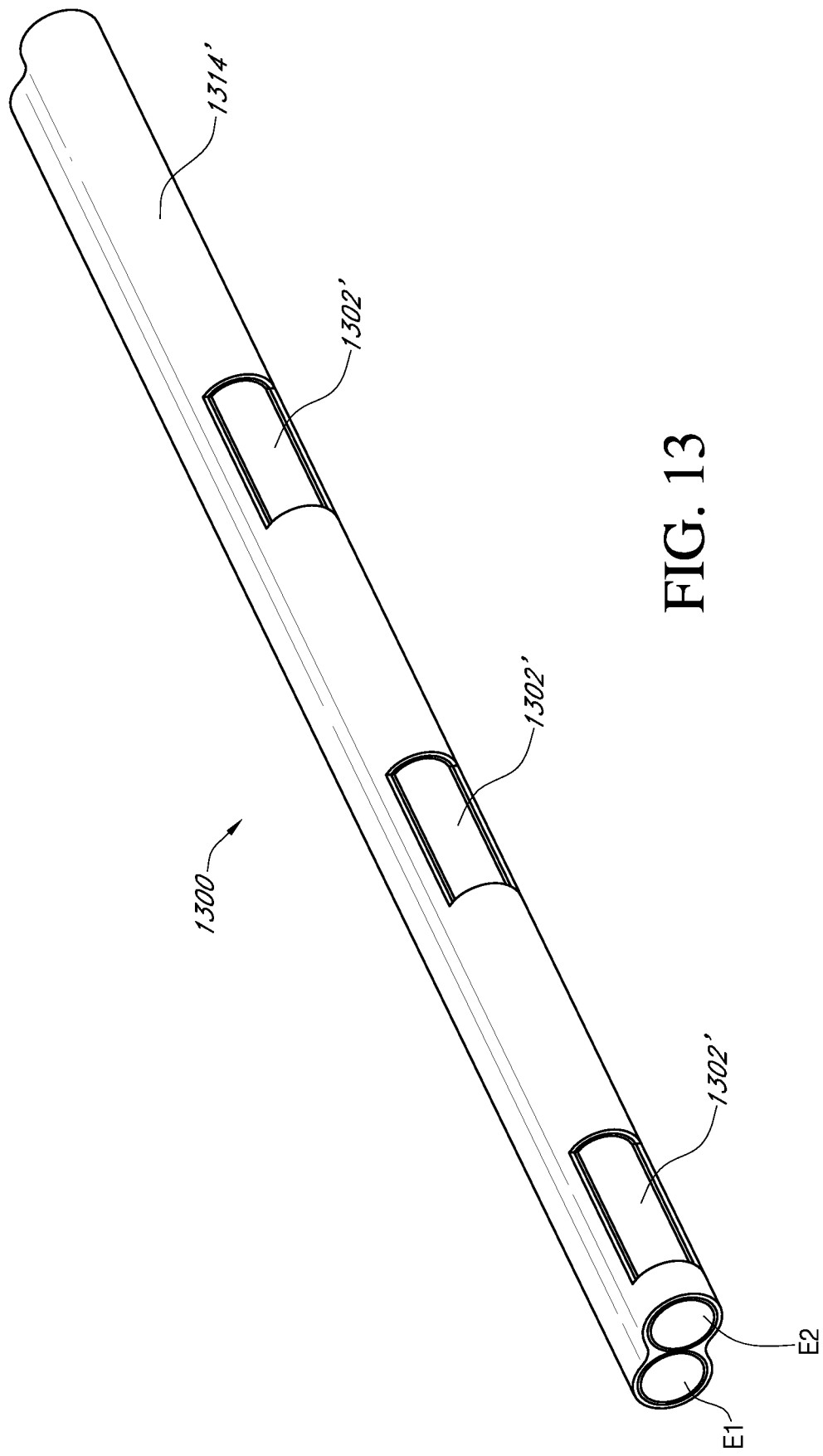
FIG. 13 is a perspective-view schematic illustrating an in vivo portion of a multi-electrode analyte sensor, with each electrode comprising a plurality of working electrodes exposed through windows.

FIG. 13 is a perspective-view schematic illustrating an in vivo portion of a multi-working-electrode analyte sensor comprising two elongated bodies E1 and E2. Each elongated body E1, E2 comprises a plurality of working electrodes (e.g., 1302') exposed through windows. The plurality of working electrodes corresponding to elongated body E1 is not shown. Windows 1302' can be formed by removing a cut portion (i.e., a cut that does not correspond to 360 degrees around the perimeter of the elongated body) of the conductive layer 1314 and a portion of the insulating layer 1304, thereby exposing electroactive surfaces of elongated bodies E1, E2. All the working electrodes 1302' share a common electrical connection through elongated body E2. The plurality of working electrodes (not shown) corresponding to elongated body E1 share a common electrical connection through elongated body E1.

By having the working electrodes dispersed at different locations of the sensor, a potential problematic situation, in which one working electrode is positioned in a location exposed to unfavorable biological activity, can be avoided. In certain embodiments, sensor data from the plurality of working electrodes in each sensor can be averaged, with suspect data from a working electrode exposed to certain undesirable biological activity thrown out.

As described elsewhere herein, the working electrodes, associated with the elongated bodies E1, E2, may each have one or more characteristics that distinguish each working electrode from the other. For example, in some embodiments, one of the working electrodes may have a membrane comprising an enzyme layer and the other working electrode may have a membrane comprising a layer having either an inactivated form of the enzyme or no enzyme.

Although not shown in FIGS. 4A-4C, the distal ends 430', 430" of the core portions of the elongated bodies E1, E2, respectively, can be covered with an insulating material (such as, for example, polyurethane or polyimide). Alternatively, one or more of the exposed core portions 430', 430" may be covered with a membrane system and serve as additional working electrodes.

Methods of fabrication of sensor systems such as those illustrated in FIGS. 3A-3C and 4A-4C are described in U.S. Patent Publ. No. 2011/0027127, which is incorporated by reference herein in its entirety.

Certain physiological responses and conditions are clinically important because such conditions can reduce sensor performance, such as by making the analyte concentration appear higher or lower than the actual concentration. For example, physiological conditions that are known to affect sensor performance include a temporary wound healing (sometimes referred to as dip and recover), biofouling, and encapsulation that lead to an effective end of life of the sensor. For example, if a host is hyperglycemic (that is, blood sugar is too high, for example, greater than about 120 mg/dl) or euglycemic (for example, blood sugar is from about 80 mg/dl to about 120 mg/dl), encapsulation can cause the host's blood sugar to appear lower than it truly is, which can lead to improper treatment decisions, such as to give the host an inadequate insulin dose. Accordingly, since certain physiological conditions can cause error and reduce sensor performance, measurement and identification of such physi-ological conditions is desirable. Physiological conditions can be identified by considering any of a variety of in vivo properties and measured parameters, such as, for example: 1) measuring $H_2O_2$; 2) measuring a constant analyte; 3) measuring impedance; 4) measuring pH; 5) measuring values at two separate electrodes; 6) analyzing processing signals; 7) evaluating $T_{90}$; 8) analyzing two sensors with different sensitivities; 9) measuring oxygen; and/or 10) measuring reference potential.

Measuring $H_2O_2$

Figure 5:
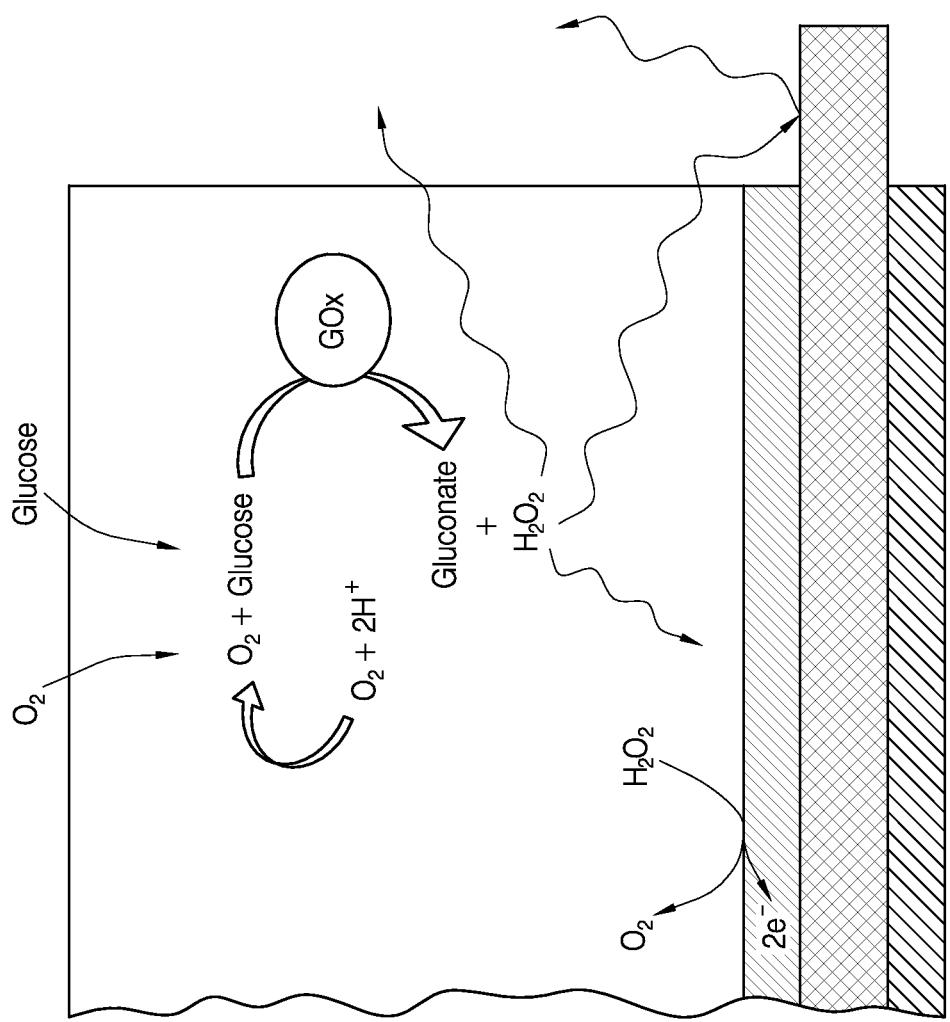
FIG. 5 is a schematic illustrating metabolism of glucose by Glucose Oxidase (GOx) and one embodiment of a diffusion barrier that substantially prevents the diffusion of $H_2O_2$ produced on a first side of the sensor.

In a typical enzymatic electrochemical sensor for detecting an analyte such as glucose, for example, the first working electrode measures the hydrogen peroxide produced by an enzyme catalyzed reaction of the analyte being detected and creates a measurable electronic current. For example, in the detection of glucose wherein glucose oxidase (GOX) produces hydrogen peroxide as a byproduct, hydrogen peroxide ($H_2O_2$) reacts with the surface of the working electrode producing two protons ($2H^+$), two electrons ($2e^-$) and one molecule of oxygen ($O_2$), which produces the electronic current being detected, as shown in FIG. 5.

In the case of glucose oxidase based analyte sensors, glucose oxidase catalyzes the conversion of oxygen and glucose to hydrogen peroxide and gluconate according to the following reaction:

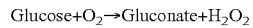

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$ (see FIG. 5). Oxidation of $H_2O_2$ by the working electrode is balanced by reduction of ambient oxygen, enzyme generated $H_2O_2$, or other reducible species at the counter electrode.

Preferably, one or more potentiostats can be employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrodes. The output signal is typically a raw data stream that can be used to provide a useful value of the measured analyte concentration in a host to the patient, doctor, or other user, for example.

The sensor electronics can be comprised of a potentiostat, A/D converter, RAM, ROM, transceiver, processor, and/or the like. The potentiostat may be used to provide a bias to the electrodes and to convert the raw data (e.g., raw counts) collected from the sensor to an analyte concentration value (such as, for example, a glucose concentration value expressed in units of mg/dL). The transmitter may be used to transmit the first and second signals to a receiver, where additional data analysis and/or calibration of analyte concentration can be processed. In certain embodiments, the sensor electronics may perform additional operations, such as, for example, data filtering and noise analysis.

A variety of devices, systems and methods can measure changes in $H_2O_2$ concentration, which in turn can assist in identifying physiological conditions around the sensor. For example, the bias potential on a working electrode can be turned off, or reduced to zero. When the electrode is turned off, $H_2O_2$ will not be reduced. When the bias potential is later turned back on, the signal achieved can be indicative of $H_2O_2$ concentration and diffusion in the area of the sensor.

As described above, the current that is produced at the working electrode is substantially proportional to the amount of $H_2O_2$ that diffuses to the working electrode. Thus, a normal signal may indicate that $H_2O_2$ is able to diffuse out of the area as expected. However, a high, sharp signal may indicate that $H_2O_2$ is unable to diffuse out of the localized area. The inability of $H_2O_2$ to diffuse out of the localized area, in turn, may indicate cessation in blood flow. This may be a strong indicator of a dip and recover physiological response. Without wishing to be bound by theory, it is believed that within a few hours to 48 hours of implantation of an implantable sensor, the body may respond to trauma by halting blood flow around the implant, which in turn results in a buildup of $H_2O_2$ near the sensor.

Accordingly, in some embodiments, a sensor can measure $H_2O_2$, and a processing module can be configured to compare $H_2O_2$ to predetermined threshold values. In some embodiments, the processing module can also process the data to identify a physiological condition or a sensor failure, as described further below. In some embodiments, the processing module can also develop a response to the identified physiological condition or sensor failure, as described further below. In some embodiments, the processing module can consider $H_2O_2$ values and can additionally consider one or more additional data inputs, such as, for example, time of day, time after implant, temperature information, or other measured parameters described herein, in identifying a physiological condition or sensor failure.

In one embodiment, because dip and recover is a temporary event that usually occurs shortly after implant, a sensor or system can be used to take measurements of $H_2O_2$ concentration and diffusion using the above-described method shortly after implantation of the device. In another embodiment, the working electrode can be switched off and on more than one time in a repetitive manner to provide multiple data points and to show a trend in $H_2O_2$ concentration and diffusion. A processing module can consider data from repetitive measurements to determine additional information, such as whether the dip and recover event is worsening or improving, for example. In some embodiments, the processing module consider whether the dip and recover event is worsening or improving to develop an appropriate response (such as, for example, any of the responses described herein).

Measuring a Constant Analyte

In some embodiments, a working electrode can be configured to generate via sensor electronics a first signal associated with both the analyte and another (or other) non-analyte (or second analyte) electroactive compound(s) that have an oxidation potential less than or similar to a first oxidation potential. An auxiliary electrode can be configured to generate a second signal associated with the non-analyte related electroactive compounds. Non-analyte related electroactive compounds can be any compound, present in the sensor's local environment, which has an oxidation potential less than or similar to the oxidation potential of the measured species (such as, for example, $H_2O_2$). While not wishing to be bound by theory, it is believed that with a glucose-measuring electrode, both the signal directly related to the enzyme-catalyzed reaction of glucose (which produces $H_2O_2$ that is oxidized at the first working electrode) and signals from unknown compounds that are in the extracellular milieu surrounding the sensor can be measured. Additional electrodes or sensors can also measure other various analytes and electroactive compounds. These analytes and compounds can be constant or non-constant (such as, for example, intermittent or transient) in concentration within the body. Measuring changes in a constant analyte can assist in identifying particular physiological conditions and sensor failure.

Second or other additional analytes or nonanalytes can be measured in any of a variety of ways. For example, in a glucose sensor, a non-glucose constant analyte can be measured, wherein the signal can be measured beneath the membrane system on the glucose sensor. While not wishing to be bound by theory, it is believed that by monitoring the sensitivity over a time period, a change associated with solute transport through the membrane system can be measured and used as an indication of a sensitivity change in the analyte measurement. In other words, a biointerface monitor can be provided, which can be capable of monitoring changes in the biointerface surrounding an implantable device, thereby enabling the measurement of sensitivity changes of an analyte sensor over time.

In some embodiments, the analyte sensor can be provided with an auxiliary electrode configured as a transport-measuring electrode disposed beneath the membrane system. The transport-measuring electrode can be configured to measure any of a number of substantially constant analytes or factors, such that a change measured by the transport-measuring electrode can be used to indicate an unusual change in analyte surrounding the sensor. Some examples of substantially constant analytes or factors that can be measured include, but are not limited to, oxygen, carboxylic acids (such as urea), amino acids, hydrogen, pH, chloride, baseline, or the like. Thus, the transport-measuring electrode provides an independent measure of changes in solute transport to the membrane, and thus sensitivity changes over time, as well as unusual in vivo conditions.

A variety of devices, systems and methods can utilize changes in constant analytes and compounds to identify physiological responses and conditions around the sensor. Because one expects certain analytes to have a constant concentration in the body, a change indicates that the host may be reacting to some stimulus or that the physiological environment around the sensor may be changing. For example, uric acid can be expected to remain relatively constant in the host. Changing measurements of a constant analyte, such as uric acid, can indicate that a physiological event such as dip and recover or encapsulation may be occurring.

In one embodiment, a glucose sensor can be configured to measure urea, which is a water-soluble constant analyte that is known to react directly or indirectly at a hydrogen peroxide sensing electrode (similar to the working electrode of the glucose sensor example described in more detail above). In one implementation wherein urea is directly measured by the sensor, the glucose sensor includes a membrane. The membrane does not, however, include an active interference domain or active enzyme directly above the sensor, thereby allowing the urea to pass through the membrane system to the electroactive surface for measurement thereon. In one alternative implementation wherein urea is indirectly measured by a sensor, the glucose sensor includes a membrane system as described in more detail above, and further includes an active uricase oxidase domain located directly above sensor, thereby allowing the urea to react at the enzyme and produce hydrogen peroxide, which can be measured at the electroactive surface thereon.

Additionally, detection of abnormal levels of any of a variety of constant analytes may be achieved by considering or processing signals associated with the constant analyte. In certain embodiments, a first sensor can be configured to measure a constant analyte (such as, for example urea or uric acid), and a processor module may be programmed to determine abnormal concentrations of the constant analyte by comparing sensor data with certain data patterns known to correspond to the analyte. In certain embodiments, a plurality of sensors can be configured to measure one or more constant analytes (such as, for example urea or uric acid), and a processor module may be programmed to determine abnormal concentrations of the one or more constant analytes by comparing sensor data with certain data patterns known to correspond to the analyte. Upon detection of abnormal levels of one or more constant analytes, processing of the data streams associated with their respective sensor element may be adjusted. In some embodiments, the processing module can process data from one or more sensors configured to measure one or more constant analytes to determine a response (such as, for example, any of the responses to physiological conditions or sensor failure described herein).

Measuring Impedance

One limitation of implantable glucose sensors is the result of differences in patient physiology that impacts sensor performances (like differences in in vitro/in vivo sensitivity), especially as they relate to tissue composition and the hydration status of the sensor's environment. Heretofore, this limitation has been one of the major challenges to creating a factory calibrated glucose sensor. For example, two sensors tested to an identical sensitivity on the bench may exhibit two very different in vivo sensitivities in two different patients (or even the same patient at two different time periods). Accordingly, this may complicate predictions of in vivo behavior based solely on bench test data alone.

Impedance measurements can also indicate certain physiological conditions within the host. In some embodiments, through use of impedance measurements, e.g., impedance measurements between the bottom surface of the sensor housing 602, 702 (skin surface) and the tip of the sensor 606, 706—individual patient physiologic information may be provided to an algorithm used to calculate analyte concentration. Such use of physiologic information can provide, to the sensor system, adjustments (e.g., adjustments to processing of sensor signal) that accounts for differences in physiology between patients. In some embodiments, sensor algorithm prediction of in vivo sensor performance is segregated by impedance states, such as high body fat, low hydration states, and/or high hydration states. This information could be used to select certain algorithm parameters/predictions states to improve accuracy and overall sensor performance and also to improve the reliability of bench data prediction of in vivo sensor use.

In some embodiments, impedance measurements can be used to detect a wound healing response, excess edema, buildup of biomaterials, or encapsulation, which in turn can be used to identify temporary or permanent loss of sensor sensitivity. Impedance measurements can also be indicative of loss of signal due to tissue compression and displacement of the sensor. In some embodiments, a single impedance measurement can be compared to known or expected impedance values to evaluate whether impedance is abnormal. Alternatively, multiple impedance measurements can be taken at varying frequencies. Additionally, multiple impedance measurements can be taken over time to monitor changes in the tissue. For example, encapsulation of the sensor by surrounding tissue can be indicated by abnormally high resistivity or increasing resistivity, and thus a high impedance value or an increase in impedance can be used to identify encapsulation tissue.

Many devices and systems can be used to measure impedance. A typical analyte sensor may have a working and reference electrode implanted into tissue, often anchored to the skin by a housing or base plate. As an example, this type of typical analyte sensor can be modified in a variety of ways to measure impedance through nearby tissue. In some embodiments, one or more additional electrodes can be placed in various positions, including for example, on the surface of the skin. The one or more additional electrodes enable measurement of electrical impedance of tissue surrounding the sensor to determine the condition of the tissue. In one embodiment, a third electrode can be placed on the surface of the skin. In some preferred embodiments, the additional electrode can be placed under the surface of the housing or base plate. In another embodiment, multiple additional electrodes can be placed on the surface of the skin, and in some embodiments all additional electrodes are located under the surface of the housing or base plate.

Figure 6:
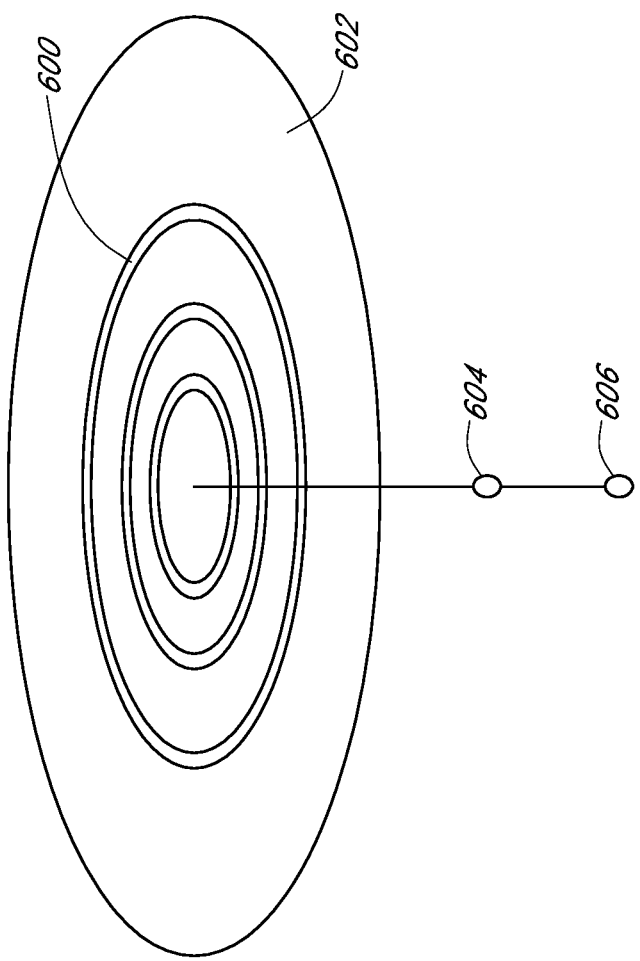
FIG. 6 is one embodiment of multiple electrodes arranged in a concentric ring pattern.
Figure 7:
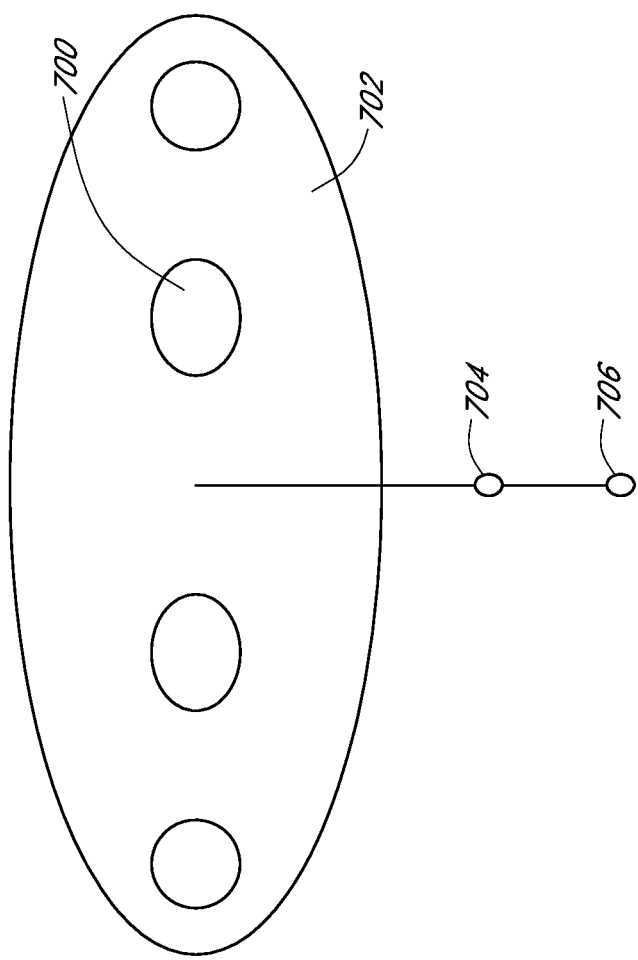
FIG. 7 is one embodiment of multiple electrodes arranged along an axis.

In another embodiment, as shown in FIG. 6, a sensor system can have additional electrodes arranged as one or more concentric substantially ring-shaped electrodes 600 on the bottom surface of the housing 602, which is situated adjacent to and in contact with the patient's skin. Reference and working electrodes, 604, 606 can extend from the bottom surface of the housing 602 and into the patient's skin. Multiple electrodes may be advantageous in certain embodiments because multiple electrodes can provide information related to the location of changes within the tissue. For example, the depth of measurement of impedance can be related to the distance between two electrodes. Thus, activation of a larger diameter ring-shaped electrode can be used to measure the impedance of tissue located at a greater radial distance away from the sensor, as compared with a smaller diameter ring-shaped electrode. A sensor system can have concentric substantially ring-shaped electrodes 600, and a processing module can be configured to compare the impedance values measured in tissues located at various radial distances from the sensor (such as, for example, values at a first outer electrode and a second inner electrode) to provide information on location of in vivo physiological changes. One of ordinary skill in the art would also appreciate that a series or group of multiple electrodes spaced apart at varying locations near the sensor can also be employed. For example, electrodes can be arranged in any concentric polygon shape, or electrodes on the skin surface can be arranged as discs placed linearly along any axis relative to the sensor, as shown in FIG. 7. As shown, a plurality of linearly placed electrodes 700 are spaced along the bottom surface of the housing 702, and working and reference electrodes 704, 706 can extend from the bottom surface of the housing 702 and into the patient's skin.

In some embodiments, the additional electrode(s) can be activated so that an impedance measurement can be made between two electrodes, e.g., one of the electrodes on the housing and in contact with the skin surface and one of the subcutaneous sensing electrodes, or two subcutaneous electrodes, or two electrodes on the skin surface. In some embodiments, one or more sensor systems can be configured to measure impedance values, and a processing module can be configured to compare the one or more impedance values to normal or expected impedance values. In some embodiments, the processing module can be further configured to process the data streams to identify a physiological condition or sensor failure, and the processing module can additionally be configured to determine a response (such as, for example, any of the responses to sensor failure described herein).

In alternate embodiments, the one or more electrodes can be activated periodically over time so as to monitor changes in tissue impedance. In some embodiments, the impedance measurements can be made and tracked over a period of minutes, hours, or days. In some embodiments, the processing module can be further configured to process the data streams to identify a physiological condition or sensor failure, and the processing module can additionally be configured to determine a response (such as, for example, any of the responses to sensor failure described herein).

In some embodiments, impedance measurements can include resistance or reactance at one frequency or at multiple frequencies, such as, for example, from about 1 kHz to about 10 MHz. Normal or expected tissue impedances are well known, and tissue impedance has a characteristic shape when resistance is plotted against reactance at multiple frequencies. Thus, by measuring impedance at multiple frequencies, the relative relationship between impedance at different frequencies may be used to determine changes in various components of the tissue. For example, an increase in fluid content can result in reduced resistance at lower frequencies, while changes in structural components (such as, for example, cell membrane changes or scar tissue buildup) may result in changes in resistance and reactance, potentially affecting the frequency at which peak reactance occurs. Accordingly, in one embodiment, a system can be configured to measure impedance at a first frequency (such as, for example, about 1 kHz, 2 kHz, 3 kHz, 4 kHz, or more) and to measure impedance at a second frequency (such as, for example, about 10 kHz, 9 kHz, 8 kHz, 7 kHz, or less), and a processing module can compare the measured impedance values. In some embodiments, each of the measured impedance values is compared to known or expected impedance values. In some embodiments, the processor module can be further configured to process the data streams to identify a physiological condition or sensor failure, and the processing module can additionally be configured to determine a response (such as, for example, any of the responses to sensor failure described herein). Information regarding known tissue impedances can advantageously be stored in or by the processor module or other sensor electronics, or can be transmitted to the processor module or other sensor electronics from a data source.

The electrical circuit required for activation and deactivation of the electrodes for measuring impedance may be arranged in any one of a variety of ways, including those known to those of skill in the art. Particularly, circuit configurations commonly used in bio-signal acquisition, such as electrocardiograms or electroencephalograms, may be useful in with the embodiments described herein. Additionally, in some embodiments, the electrical circuit may use mechanical or solid state relays, and in some preferred embodiments the mechanical or solid state relays have low capacitance. The one or more electrodes located away from the sensor, such as on the skin surface, may also be used as a grounding plane to enable significantly improved common mode noise rejection by using the inputs from the reference and working electrodes as inputs to a differential mode amplifier.

Measuring pH

In some embodiments, pH measurements can be obtained in areas adjacent to an implantable sensor. In some embodiments, a separate pH detector is used to detect abnormal pH in areas adjacent to the sensor. In some embodiments, a sensor system can be configured to measure pH. pH values can indicate changes in physiologic conditions and may help identify sensor failure. For example, tissue pH is typically around 7.4, and a decrease in pH can indicate a reduction in tissue perfusion and lack of blood flow in the area. Such reduction in tissue perfusion, in turn, can indicate the presence of dip and recover.

Accordingly, in some embodiments, a sensor or pH detector can measure pH and a processing module can be configured to compare pH values to predetermined threshold values. In some embodiments, the processing module can also process the data to identify a physiological condition or a sensor failure. In some embodiments, the processing module can also develop a response to the identified physiological condition or sensor failure, as described further below. In some embodiments, the processing module can consider pH values and can additionally consider one or more additional data inputs, such as, for example, time of day, time after implant, or other measured parameters described herein, in identifying a physiological condition or sensor failure. In some embodiments, the processing module can consider pH values and other additional data inputs in identifying a physiologic condition or sensor failure, such as, for example, depth of insertion and/or temperature and/or pressure, all of which can affect pH values.

Measuring Values at Two Electrodes that are not Collocated

A device or system incorporating a plurality of electrodes can also be used to measure in vivo properties. Multiple electrodes can be arranged in variety of ways, including those described in U.S. Patent Publ. No. 2011/0024307 and U.S. Patent Publ. No. 2011/0027127, filed Jul. 1, 2010, which are incorporated by reference herein in their entirety. Additionally, the sensors described in the above-identified applications are not inclusive of all applicable analyte sensors, and it should be understood that the embodiments disclosed herein are applicable to a variety of analyte sensor configurations.

In some embodiments, the electrodes can be positioned so that they are not collocated, such that the electrodes are not substantially affected by the presence of the other electrodes or are not substantially affected by a wound response to the other electrodes, for example. By way of example, in certain embodiments the electrodes can be positioned at a distance from each other, e.g., about 0.01 inches or more away from each other, 0.02 inches or more away from each other, 0.03 inches or more away from each other, 0.04 inches or more away from each other, 0.05 inches or more away from each other, 0.06 inches or more away from each other, 0.07 inches or more away from each other, 0.08 inches or more away from each other, 0.09 inches or more away from each other, 0.1 inches or more away from each other, 0.11 inches or more away from each other, 0.12 inches or more away from each other, 0.13 inches or more away from each other, 0.14 inches or more away from each other, 0.15 inches or more away from each other, 0.16 inches or more away from each other, 0.17 inches or more away from each other, 0.18 inches or more away from each other, 0.19 inches or more away from each other, 0.2 inches or more away from each other, 0.3 inches or more away from each other, 0.4 inches or more away from each other, 0.5 or more inches away from each other, 1 or more inches away from each other, 2 or more inches away from each other, 3 or more inches away from each other, 4 or more inches away from each other, or 5 or more inches away from each other.

In some embodiments, a plurality of electrodes can be arranged as one or more concentric substantially ring-shaped electrodes on the bottom surface of a sensor housing, such as illustrated by the embodiment in FIG. 6. One of skill in the art can also appreciate that a series or group of multiple electrodes spaced apart at varying locations relative to the sensor housing can also be employed. For example, electrodes can be arranged in any concentric polygon shape, in one embodiment. In another embodiment, electrodes can be arranged as discs placed linearly along any axis relative to the sensor, as illustrated in FIG. 7. In other embodiments, two or more sensors, each with its own housing or base plate, can be implanted at any location in the abdomen, or other location in the host's body. In some embodiments, the two or more sensor housings can be implanted apart from each other, e.g., 0.5 or more inches away from each other, 1 or more inches away from each other, 2 or more inches away from each other, 3 or more inches away from each other, 4 or more inches away from each other, or 5 or more inches away from each other.

The values and signals detected by the two or more separate (i.e., not collocated) electrodes can provide various information useful for measuring a physiological condition around the sensor. In one embodiment, a system can have a plurality of separate sensors located such that they are independently influenced by in vivo conditions, wherein each sensor can measure or detect a parameter (such as, for example, analytes, pH, impedance, temperature, or other parameters mentioned herein), and a processing module can consider the data inputs from each sensor to identify a physiological condition or a sensor failure related to at least one of the sensors. For example, if one sensor detects glucose values within a normal range, but the other sensor detects abnormal glucose values outside of the normal range, a dip and recover response or biofouling or encapsulation may be occurring at one of the electrode sites. In some embodiments, a processing module can be configured to determine a response to the identified physiological condition or sensor failure (such as, for example, any of the responses to sensor failure described herein). Additionally, systems comprising separated (i.e., not collocated) sensors can be used to determine confidence levels in measured values or data. For example, if both sensors provide the same data, then the confidence level in the results increases. The electroactive regions of separate sensors can be spaced apart from each other by a distance. In some embodiments, a spacing between the electroactive regions of separate sensors is 0.1 mm or more, 0.2 mm or more, 0.3 mm or more, 0.4 mm or more, 0.5 mm or more, 0.6 mm or more, 0.7 mm or more, 0.8 mm or more, 0.9 mm or more, 1 mm or more, 1.1 mm or more, 1.2 mm or more, 1.3 mm or more, 1.4 mm or more, 1.5 mm or more, 1.6 mm or more, 1.7 mm or more, 1.8 mm or more, 1.9 mm or more, 2 mm or more, 2.25 mm or more, 2.5 mm or more, 2.75 mm or more, 3 mm or more, 3.25 mm or more, 3.5 mm or more, 3.75 mm or more, 4 mm or more, 4.25 mm or more, 4.5 mm or more, 4.75 mm or more, 5 mm or more, 6 mm or more, 6.5 mm or more, 7 mm or more, 7.5 mm or more, 8 mm or more, 8.5 mm or more, 9 mm or more, 9.5 mm or more, or 10 mm or more. Typically, the spacing is from 0.1 to 10 mm.

Measuring Values at Two Sensors with Varying Sensitivities

As described above, a device or system having one or more sensors can be used to measure an in vivo property. In addition to using multiple identical sensors, multiple sensors configured to have varying characteristics, such as for example, varying sensitivities to glucose can be employed. Sensor sensitivity can vary based on different membranes, different interferent domains, and different enzyme layers, among others. The various ways in which sensors having different sensitivities can be formed and utilized is described in U.S. Patent Publ. No. 2011/0024307 and U.S. Patent Publ. No. 2011/0027127, which are incorporated by reference herein in their entirety.

In some of these embodiments, the sensitivity or current density (i.e., sensitivity divided by surface area of the electroactive surface) of one or more of the sensor elements is substantially higher than the sensitivities or current densities of other sensor elements, but in other embodiments, the sensitivities or current densities of the sensor elements are substantially equal. In some embodiments, the sensor system includes a first sensor element having a first sensitivity and a second sensor element having a second sensitivity, wherein the first sensitivity is higher than the second sensitivity. In some embodiments, the first sensitivity is from about 1 pA/mg/dL to about 100 pA/mg/dL, or from about 1 pA/mg/dL to about 25 pA/mg/dL, and the second sensitivity is from about 20 pA/mg/dL to about 300 pA/mg/dL, or from about 50 pA/mg/dL to about 100 pA/mg/dL. In some embodiments, the sensor system includes a first sensor element having a first current density and a second sensor element having a second current density, wherein the first current density is higher than the second current density. In some of these embodiments, the current density of the first element is from about 3 pA/mg/dL/mm$^2$ to about 325 pA/mg/dL/mm$^2$, or from about 3 pA/mg/dL/mm$^2$ to about 85 pA/mg/dL/mm$^2$, and the current density of the second element is from about 65 pA/mg/dL/mm$^2$ to about 1,000 pA/mg/dL/mm$^2$, or from about 165 pA/mg/dL/mm$^2$ to about 1,700 pA/mg/dL/mm$^2$.

In some embodiments, the sensor element with the higher sensitivity or higher current density is used to measure or provide output at low glucose concentration ranges, while the sensor element with the lower sensitivity or lower current density is used to measure or provide output at high glucose concentration ranges. Advantageously, in some embodiments, improved glucose concentration measurement accuracy at both low and high glucose levels is achieved by configuring the first sensor element to have a higher sensitivity or higher current density and the second to have a lower sensitivity or lower current density.

Sensor sensitivity can change over time. Therefore, in some embodiments, two or more glucose sensors with varying sensitivities can be used to detect abnormal sensitivity changes. In some embodiments, a known relationship is defined between the first and second sensor elements, for example a relationship between the sensitivities or current densities of the first and second sensor elements, which is determined from prior in vitro and/or in vivo data. A processing module can be configured to compare and analyze data from the two sensor elements and can identify abnormal pattern of sensitivity change, which in turn can be indicative of a physiological condition or sensor failure.

As described elsewhere herein, in some embodiments, a processing module can be configured to compare and analyze signals. The comparison and analysis can include integrating or averaging signals from a plurality of sensor elements. In some embodiments, the processing module may be configured to compare and analyze sensor data, identify a physiological response, and determine a response (such as, for example, any of the responses described elsewhere herein). Additionally, in sensor systems having two or more sensors with different sensitivities, the processing module may be configured consider other data streams (such as oxygen levels), and may be configured to accord less (or no) weight to a high sensitivity sensor element, as compared to a low sensitivity sensor element, in environments associated with low oxygen and high glucose concentration, for example. Conversely, the processing module may be configured to accord more weight to the high sensitivity sensor element in environments associated with high oxygen and low glucose concentration, for example. As an alternative to weighting, the processing module may be configured to poll sensor data from the low glucose sensitivity sensor only when an environment associated with a low oxygen environment is detected.

In some embodiments, signals received from the two sensor elements can be compared and analyzed to provide information not only about glucose concentration, but information about other parameters that indicate physiological conditions and/or can affect sensor performance. For example, during a sensor session, if the oxygen level near the sensor elements diminishes below a certain level, the high sensitivity sensor element may no longer be accurate. Under these conditions, the high sensitivity sensor may become noisy and thus become less accurate, while the low sensitivity sensor element can continue to measure accurately. Accordingly, in some embodiments in which comparison and analysis of signals is made by integrating or averaging signals from a plurality of sensor elements, the sensor electronics may be configured to accord less (or no) weight to a high sensitivity sensor element, as compared to a low sensitivity sensor element, in environments associated with low oxygen and high glucose concentration. Conversely, the sensor electronics may be configured to accord more weight to the high sensitivity sensor element in environments associated with high oxygen and low glucose concentration. As an alternative to weighting, the sensor electronics may be configured to poll sensor data from the low glucose sensitivity sensor only when an environment associated with a low oxygen environment is detected.

In some embodiments, the noise that may be present in data from a high sensitivity sensor element (e.g., one in the presence of a low oxygen environment) may provide an indication that a low glucose sensitivity sensor is approaching an environment in which it may also become inaccurate as well. Accordingly, the processing module may be configured to monitor, on the high sensitivity sensor element, a noise pattern that corresponds to a low oxygen environment. Following detection of the noise pattern, the sensor electronics can be instructed to poll data from the low sensitivity only, or alternatively adjust the weight accorded to the high sensitivity sensor with respect to the low sensitivity sensor.

While not wishing to be bound by theory, it is believed that oxygen availability typically decreases with time during the age of a sensor, as the amount of oxygen that can be transported across the membrane of a sensor element diminishes. While not wishing to be bound by theory, it is believed that this phenomenon may be attributed at least in part to the body's response to a foreign object (e.g., a continuous glucose sensor), whereby barrier cells are formed surrounding the sensor elements, resulting in biofouling or eventually end of life of the sensor. Over time, the barrier cells reduce or completely block the transport of oxygen across the membrane of the sensor elements. In some embodiments, the sensor system is formed with a high sensitivity or high current density sensor element that provides greater accuracy during a large duration of the sensor system's life, and a low sensitivity or low current density sensor element that provides better low oxygen performance, and thus can be used near the end of the sensor system's life. In some embodiments, the sensor system formed with at least one high sensitivity sensor and at least one low sensitivity sensor can provide data inputs that can be used by the processing module to identify end of life of the sensor. In some embodiments, the processing module can additionally be configured to respond to the identified physiological condition or sensor failure (such as, for example, in any of the ways described elsewhere herein).

Measuring T90 of Constant Analyte

As described above, sensor systems can be configured to measure one or more constant analytes. Additionally, sensor systems can be configured to measure and monitor response times for the one or more constant analytes. Response time is often specified in terms of the time to reach 90% of its final reading and is therefore known as a T90 value. Thus, a sensor system can monitor a T90 value for one or more constant analytes to identify certain in vivo physiological conditions. For example, where there is no biofouling or encapsulation present, the sensor functions more rapidly (that is, T90 is reached more rapidly).

In some embodiments, a sensor system can include one or more sensors configured to measure one or more constant analytes, and a processing module can process the data to calculate the T90 value for each measured constant analyte. In some embodiments, the processing module can be configured to compare the T90 data to known or in vitro response time, and can determine if there is an abnormal response time. In some embodiments, the processing module can compare the data to previous measurements in the same sensor session. In some embodiments, the processing module can be configured to identify a physiological condition or sensor failure. In some embodiments, the processing module can additionally be configured to respond to the identified physiological condition or sensor failure (such as, for example, in any of the ways described elsewhere herein).

Measuring Oxygen and Baseline Current

In some embodiments, the analyte sensor can be configured to measure a signal associated with a constant non-analyte, or other analyte in addition to the primary analyte being monitored. In some preferable embodiments, the signal for the constant non-analyte or analyte can be measured beneath the membrane system on the sensor.

In one example of a glucose sensor, a non-glucose constant that can be measured is oxygen, wherein a measured change in oxygen transport can be indicative of a change in the sensitivity of the glucose signal. As described elsewhere herein, certain enzyme-based sensors (e.g., glucose-oxidase-based sensors) are limited by the amount of oxygen present in the sensor environment. When the oxygen level reduces below a threshold value, the enzyme-containing working electrode can drop due to oxygen starvation, even though the glucose concentration is constant. This oxygen starvation can occur late in the sensor life, when the sensor is encapsulated in the subcutaneous environment. Being able to measure oxygen thus may allow for the detection of this encapsulation and (by extension) the end of the sensor's life.

A change in oxygen can be indicative of various physiological responses or conditions in the body. The oxygen level can be measured using any one of a variety of devices, systems, and methods, including those known to those of skill in the art. In some particular embodiments, the oxygen level can be measured by switching the bias potential of the working electrode, using an auxiliary oxygen-measuring electrode, or an oxygen sensor, or the like. Alternatively, oxygen can be measured using pulsed amperometric detection on the glucose-measuring working electrode (eliminating the need for a separate auxiliary electrode). In another embodiment, the auxiliary electrode can be configured specifically as an oxygen-measuring electrode. In another embodiment, an oxygen sensor can be added to the glucose sensor, as is appreciated by one skilled in the art, eliminating the need for an auxiliary electrode Some preferred embodiments use the existing structure of a dual electrode analyte sensor, such as those described above, to measure oxygen levels. Glucose oxidase based sensors are limited by the amount of oxygen present. When the oxygen level reduces below a threshold value, the enzyme electrode current drops ("oxygen starvation") while the glucose concentration is constant; therefore, oxygen starvation results in reduced accuracy as lower than actual glucose values are reported by the sensor system. Oxygen starvation can occur when the sensor becomes encapsulated in the subcutaneous environment, for example. Thus, separately measuring oxygen levels at the sensor allows for identification of encapsulation.

In order to use the non-enzyme electrode as an oxygen sensor, in some embodiments, the bias potential of the non-enzyme electrode can be changed from a positive value (typically about 600 mV-800 mV) to a negative value (typically about negative 600 mV-800 mV). At this potential, dissolved oxygen can be reduced and gives rise to a negative current through the non-enzyme electrode. Switching the bias potential in this manner results in a bifunctional electrode. When the positive bias is applied, the current is related to a baseline current. When the negative bias is applied, the current is related to the local oxygen concentration.

In yet another embodiment, oxygen concentration can be measured by applying a negative bias potential to the non-enzyme electrode and subsequently intentionally depleting the local oxygen concentration. Depletion can occur as oxygen is electrochemically removed as a result of the oxygen measurement process, and the enzyme electrode measuring the glucose levels will be affected by the oxygen depletion. If the oxygen level prior to intentional depletion is close to the threshold value, then the intentional depletion will reduce the dissolved oxygen below the threshold value described above, which will result in a sudden drop in enzyme electrode current. On a sliding scale, the earlier the drop in enzyme electrode occurs after applying the negative bias, the closer the oxygen concentration is to the threshold value. Alternatively, if no drop occurs within a predetermined time window, it can be concluded that the oxygen level is above the threshold value at the sensor location. In some cases, this intentional depletion method may be preferable because it provides information on whether the particular sensor is oxygen starved or not, rather than only measuring the oxygen concentration in the area of the sensor. In vivo oxygen measurements as described above can be valuable for many reasons, including indicating encapsulation of the sensor. For example, when the sensor is encapsulated, oxygen levels are low.

As described elsewhere herein, in some embodiments, after a low oxygen level is detected signaling the possibility of an impending end of sensor life, the sensor system may apply appropriate measures, such as, temporarily invalidating or blanking the displayed glucose values, initiating an alarm, or instructing the user to certain actions that may increase oxygen concentration to the sensor surrounding. If after a predetermined time period the low oxygen condition persists, the sensor system may instruct the user to replace the sensor and/or automatically shut off, either temporarily or permanently.

Thermistor

In some embodiments, a thermistor can be used to identify physiological conditions or sensor failure. In one embodiment, a thermistor can be used in a "self-heating mode" whereby a thermistor is heated to a specific temperature (such as for example, 1, 2, 3, 4, 5 or more degrees Celsius above normal temperature for a period of about 1, 2, 3, 4, 5, or more seconds). In some embodiments, the thermistor can be heated in a pattern (such as, for example, a sinusoidal pattern). In some embodiments, the thermistor used has a resistance of from about 1 kOhm to about 2 kOhm. The processing module can process data from the thermistor, and can determine tissue properties or sensor failure based on decrease in temperature or phase changes in tissue surrounding the thermistor as compared with known or expected values. For example, certain decay waveforms indicate the presence of edema or higher blood flow to the sensor area, which in turn indicates encapsulation, inflammation, or compression in the area of the sensor. In some embodiments, the processing module can additionally be configured to respond to the identified physiological condition or sensor failure (such as, for example, in any of the ways described elsewhere herein).

Identifying Physiological Response or Condition

Several various physiological conditions are clinically important, and specific conditions can be identified using one or more of the above measurements. It is particularly relevant to identify and differentiate dip and recover, biofouling, and encapsulation or end of life conditions or events. In addition to other relevant uses, identification of the specific condition can be useful for determining the appropriate response that should be taken by the patient, doctor, other user, or system. For example, a dip and recover response may require that the patient wait until the temporary event resolves, while encapsulation may require that the patient replace the sensor with a new sensor.

In certain embodiments, one measured in vivo property can be considered to identify the physiological response or condition within the body. In other embodiments, multiple measured properties are considered equally to identify the physiological condition within the body. In yet other embodiments, multiple measured properties are considered and weighted based on various factors to identify the physiological condition within the body. In certain embodiments, any measured parameter described herein can be considered and/or compared, along with any other measured parameter mentioned herein and/or with additional information (such as, for example, time of day, time after implant, temperature data) to identify a physiological condition or sensor failure.

A processing module can be programmed to process and compare data in any of a variety of ways. In some embodiments, the magnitudes of two or more signals are compared. The processor can also be programmed to recognize that one or more deviations over a certain threshold (such as, for example, deviations of 1%, 2%, 5%, or 10% or more) between each sensor's measurements of various parameters may be indicative of a physiological condition or sensor failure. For example, if the impedance is 5% higher than expected values, then an abnormal physiological condition is indicated and/or one or more of the sensors can be considered failed, in some embodiments.

In certain embodiments, one or more measured in vivo properties can be used to identify a temporary wound healing response, termed dip and recover. Without wishing to be bound by theory, it is believed that dip and recover may be triggered by trauma from insertion of the implantable sensor, and possibly from irritation of the nerve bundle near the implantation area, resulting in the nerve bundle reducing blood flow to the implantation area. Alternatively, dip and recover may be related to damage to nearby blood vessels, resulting in a vasospastic event. Any local cessation of blood flow in the implantation area for a period of time leads to a reduced amount of glucose in the area of the sensor. During this time, the sensor has a reduced sensitivity and may be unable to accurately track glucose. Thus, dip and recover typically manifests as a suppressed glucose signal. Dip and recover often appears within the first day after implantation of the signal, most commonly within the first 12 hours after implantation. Importantly, dip and recover normally resolves within 6-8 hours. Identification of dip and recover can provide information to a patient, physician, or other user that the sensor is only temporarily affected by a short-term physiological response, and that there is no need to remove the implant as normal function will likely return within hours.

Many of the above-described measurements may be relevant to identification of a dip and recover phenomenon. For example, a spike in an $H_2O_2$ signal after the bias potential of the electrode is shut off and on may indicate that a dip and recover condition exists. Additionally, a change in the amount of a constant analyte may indicate a dip and recover condition exists. Specifically, when the concentration of a typically constant analyte drops, it is suspected that blood flow to the sensor region is reduced as occurs with dip and recover. The time after implant can also be considered when identifying dip and recover. In some embodiments, several measurements can be considered together, and in other embodiments, several measurements can be considered and weighted appropriately.

In certain embodiments, one or more measured in vivo properties are used to identify biofouling. During wound healing and foreign body response, the surface of the implantable sensor can become coated in protein or other biological material to such an extent that the sensor is unable to accurately track blood glucose. This phenomenon is sometimes called biofouling, which often manifests itself as a downward shift in sensor sensitivity over time.

Many of the above-described measurements may be relevant to identification of biofouling. For example, impedance measurements can be used to determine whether there is buildup of biological material on the sensor, and such measurements can indicate the extent of build up as well. Impedance measurements can be made at various locations in and around the sensor area, and can be made over time to provide information on whether the biofouling condition is improving or worsening.

In certain embodiments, one or more measured in vivo properties are used to identify encapsulation that has resulted or will result in effective end of life of the sensor. An implantable sensor can become encapsulated by biological material to such an extent that the sensor is substantially unable to provide glucose data, and the sensor is considered to effectively be at end of life. Many of the same measurements useful for the identification of biofouling may be relevant to identification of the end of sensor life. For example, impedance measurements can be used to determine the sensor is being encapsulated by tissue. Impedance measurements can be made at various locations in and around the sensor area, and can be made over time to provide information on whether the encapsulation condition is worsening. In other embodiments, two sensors with different sensitivities can be used to evaluate whether encapsulation is occurring.

A processing module, or sensor electronics, can be used to determine and identify the type of physiological condition or sensor failure present. The sensor electronics may include a potentiostat, A/D converter, RAM, ROM, transceiver, processor, and/or the like. The potentiostat may be used to provide a bias to the electrodes and to convert the raw data (e.g., raw counts) collected from a sensor to an analyte concentration value (such as, for example, a glucose concentration value expressed in units of mg/dL). The transmitter may be used to transmit a first and second signal (or additional signals) to a receiver, where additional data analysis and/or calibration of analyte concentration can be processed. In certain embodiments, the sensor electronics may perform additional operations, such as, for example, data filtering and noise analysis.

Response to Physiological Condition

Identification of the physiological condition surrounding the sensor allows a system, patient, doctor, or other user to respond appropriately to the identified condition. In some embodiments, the system, patient, doctor, or other user can take steps to compensate for or correct the identified condition. There are many appropriate responses to the various physiological conditions that can occur near the implantable sensor. For example, the system can automatically shut off the sensor, either temporarily or permanently. Additionally, the system can provide an audible or visual alarm, or provide various audible or visual information or instructions to the user, such as directing the user to wait an appropriate amount of time or directing the user to change sensors. In other embodiments, the system can respond by calibrating or compensating in some way for the identified condition, or the system or user can respond by correcting the physiological condition through various means. In some embodiments, for example, the system or user can respond by applying energy to the surface of the skin to break up the identified encapsulation tissue. In a closed loop system, the system can respond by supplying insulin.

In some embodiments, after dip and recover conditions are identified, the system can notify a user to use another method to monitor blood glucose levels temporarily until the condition resolves. For example, the sensor system can notify the user that sensor data are temporarily affected by implantation of the device, and that glucose should be monitored by another method in the interim. In another embodiment, the system can provide information describing the patient's physiological condition or otherwise explaining the cause of the interruption in sensor function. In one embodiment, the sensor system can display an estimated time at which the sensor will likely function properly again. In one embodiment, the sensor system can completely cease display of data. In another embodiment, the system can provide a message, sound an alarm, or otherwise notify the user when the dip and recover event has resolved and that the sensor is functioning properly again. In some embodiments, the sensor system can notify or inform the user through a visually displayed message on a user interface, and in other embodiments, the system can notify or inform the user through audible alarms or messages. In some embodiments, the sensor system can notify or inform the user through a combination of both visual and audible alarms or messages.

After certain physiological conditions are identified, such as biofouling or encapsulation, the sensor may no longer be reliable, providing inaccurate sensor data. To prevent further use of the unreliable sensor, some embodiments notify a user to change the sensor after it has been determined that the sensor should no longer be used. Once it is determined that the sensor should no longer be used, the sensor system can notify a user that a new sensor should be implanted by audibly and/or visually prompting a user to use a new sensor and/or shutting down a display or ceasing to display sensor data on the display, for example. The alarm can also inform the user why sensor reuse may be undesirable, such as potentially providing inaccurate and unreliable sensor readings. Identification of biofouling or end of life can alternatively or additionally cause the sensor system to fully or partially shut down and/or cease display of sensor data on a user interface of the sensor system. Continuing to use the sensor once biofouling or encapsulation resulting in end of life is detected, can be dangerous to the user because the sensor may provide inaccurate data upon which the user may rely. In some embodiments, the implantable device can also be programmed to initiate action to correct for errors associated with biofouling and end of life, so that identification of these phenomena also aids in providing more accurate glucose data, or to initiate action to mitigate biofouling so as to provide more accurate glucose data.

In some embodiments, a receiver, which can also include a display device or user interface, can be in communication (e.g., wired or wireless) with an electronics module, which can often be within the sensor housing. The receiver can be an application-specific hand-held device, or a general purpose device, such as a personal computer (PC), smart phone, tablet computer, and the like. In one embodiment, a receiver can be in data communication with the sensor housing for receiving sensor data, such as raw and/or displayable data, and include a processing module for processing and/or display the received sensor data. The receiver can also and include an input module configured to receive input, such as calibration codes, reference analyte values, and any other information discussed herein, from a user via a keyboard or touch-sensitive display screen, for example, and can also be configured to receive information from external devices, such as insulin pumps and reference meters, via wired or wireless data communication. The input can be processed alone or in combination with information received from the sensor electronics module. The receiver can be programmed to notify or inform the user in the various ways described above, such as, for example displaying messages or visual information, providing audible instructions, and/or sounding alarms.

In some embodiments, the sensor system can provide a quality score, which can be indicative of sensor reliability, accuracy, and sensor failure. A quality score can be determined by considering any measured parameters described herein, and additional information (such as, for example, time of day or time after implant, etc.). In some embodiments, the quality score can be a numerical value. Although various scales can be used for the quality score, in one embodiment, a score of 100 can indicate perfect tracking for all measured parameters.

Some embodiments can include a closed loop analyte sensor system, wherein the system uses one or more sensors to measure in vivo parameters and calculate analyte values, and wherein the system can deliver an appropriate amount of a fluid to the patient (such as, for example, through a pump). Such closed loop systems can monitor and control analyte values in a host. In some embodiments, the analyte measured is glucose, and the fluid delivered is insulin. In some embodiments of a closed loop system, a quality score can be considered by the system in determining a response. In some embodiments, of a closed loop system, a quality score can be considered by the system to control the analyte to a target value. In other embodiments of a closed loop system, a quality score can be considered by the system to control the analyte to a target range of values. For example, if the quality score is high, a closed loop system can respond by controlling the analyte (such as, for example, glucose) to a target value (such as, for example, 72 mg/dL), in some embodiments. In other embodiments, the system can respond by controlling the analyte (such as, for example, glucose) to a narrow target range (such as, for example, from about 70 mg/dL to about 100 mg/dL). A high quality score value is a relative term and depends on the scale used; however, in one embodiment where 100 indicates perfect tracking, a high quality score may be any score above 60, 65, 75, 80, 85, 90, or 95.

In some embodiments, for example, if the quality score is at a medium level, the closed loop system can respond by controlling the analyte (such as, for example, glucose) to a broad target range (such as, for example, from about 70 mg/dL to about 1030 mg/dL), in some embodiments. A medium quality score value is a relative term and depends on the scale used; however, in one embodiment where 100 indicates a perfect tracking, a medium quality score may be any score between about 20-95, 35-85, 45-75, 55-65, or about 50 or about 60.

In certain embodiments, if the quality score is low, the closed loop system can respond by controlling the analyte (such as, for example, glucose) to a broad target range (such as, for example, from about 65 mg/dL to about 150 mg/dL). In some embodiments, the system can respond by instructing or notifying the user to use alternative methods (such as, for example, finger prick method) to monitor analyte levels. The system can also respond by temporarily or permanently suspending the closed loop system, for example. The system can also respond to a low quality score in other various ways, as further described below with respect to sensor failure. A low value is a relative term and depends on the scale used; however, in one embodiment where 100 indicates a perfect tracking, a low quality score may be any score below 5, 10, 15, 20, 25, 30, 35, 40, 45, or 50, in some embodiments.

While the above examples discuss closed loop analyte sensor systems, quality score data can be utilized as part of a semi-closed loop system and by any analyte sensor systems. For example, a semi-closed loop system can operate by suspending fluid delivery when analyte levels are at a certain level or within a certain range of values. In some semi-closed loop systems, the fluid delivered is insulin and the analyte measured is glucose. In some embodiments of a semi-closed loop system, a quality score can be considered by the system in determining a response. In some embodiments, of a semi-closed loop system, a quality score can be considered by the system to control the analyte to a target value. In other embodiments of a closed loop system, a quality score can be considered by the system to control the analyte to a target range of values. In some semi-closed loop systems, the quality score can be considered by the system to suspend delivery of a fluid until measured analyte values are within a certain target range. Quality score data can also be utilized by other analyte sensors, such as, for example, sensors that measure analyte values and/or provide data to a user. In some embodiments, quality score data can be considered by an analyte sensor in determining an appropriate response. For example, in some embodiments, a low quality score (as defined above), can prompt a system to notify or instruct a user to use an alternative analyte sensing method due to sensor failure. In other embodiments, the quality score can be provided to a user to inform the user as to the reliability of sensor data.

The quality score can be calculated in any of a variety of ways. In one embodiment, measured parameters are compared to known or in vitro values. In one embodiment, a parameter measured by a first sensor is compared to a parameter measured by a second sensor. In one embodiment, multiple parameters measured by the first sensor are compared to multiple parameters measured by the second sensor. In certain embodiments, one or more of the measured parameters are weighted in calculating the quality score. For example, the magnitude between the two or more sensor's amplitude, sensitivity, change in sensitivity, baseline, change in baseline, or various scaled raw signals can be considered. In some embodiments, an algorithm may be applied to the sensor data to calculate the quality score.

Once calculated, the quality score can be provided to the user or can be used by the system to develop an appropriate response, as described above. In addition to aiding in monitoring and controlling or partially controlling fluid delivery in closed loop or semi-closed loop systems, the quality score can be utilized to determine or select any of a variety of appropriate responses. For example, in some embodiments, the system can automatically shut off the sensor, either temporarily or permanently. Additionally, the system can provide an audible or visual alarm. In some embodiments, the system can provide various audible or visual information, such as a numerical quality score indicator to inform the user as the reliability of the analyte measurements. In some embodiments, the system can provide instructions to the user, such as directing the user to wait an appropriate amount of time or directing the user to change sensors. In some embodiments, the system can provide instructions to the user to use an alternative method to measure analyte values (such as, for example, a finger prick method). In other embodiments, the system can respond by re-calibrating or compensating in some way.

Additionally, the techniques described herein can be used to generate calibration information (such as, for example, one or more of baseline, sensor sensitivity, and temperature information) that can in turn be used to form or modify a conversion function, or calibration factor, used to convert sensor data (e.g., in units of electrical current) into blood glucose data (such as, for example, glucose concentration values in units of mg/dL or mmol/L).

Figure 10:
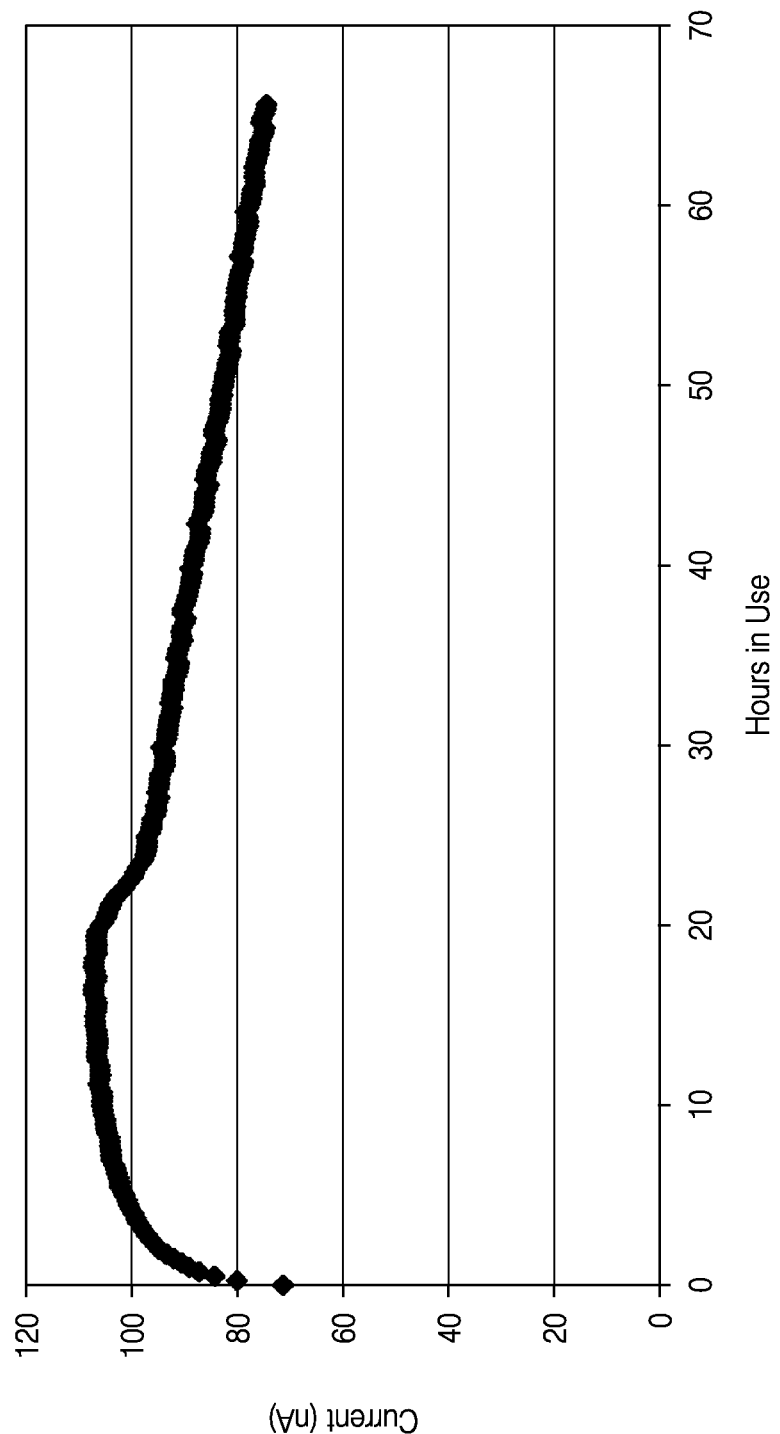
FIG. 10 is a plot of a drop in response of a particular sensor at a constant glucose concentration over time.

In some embodiments, the sensor comprises an enzyme that reacts with the analyte to be measured, and the byproduct of the reaction is qualified or quantified at the electrode. Such sensors can employ a silver/silver chloride reference electrode. Over time, such a reference electrode can become depleted when silver chloride is converted to silver metal and chloride ion. When silver chloride is depleted, the reference electrode capacity decreases. After a certain level of depletion, the reference electrode's stability will be noticeably reduced such that the glucose sensor (of which the reference electrode is part of) becomes less linear. FIG. 10 is a plot of a signal response of a glucose sensor at a constant glucose concentration of 400 mg/dL. As illustrated in FIG. 10, current can drop, e.g., between about 20 and about 22.5 hours with the glucose sensor producing the sensor data from which the plot was derived—over time when the reference electrode becomes depleted. Because the sensor is in a constant glucose concentration of 400 mg/dL for the test, the decrease in current also indicates a sensitivity drop.

Figure 11:
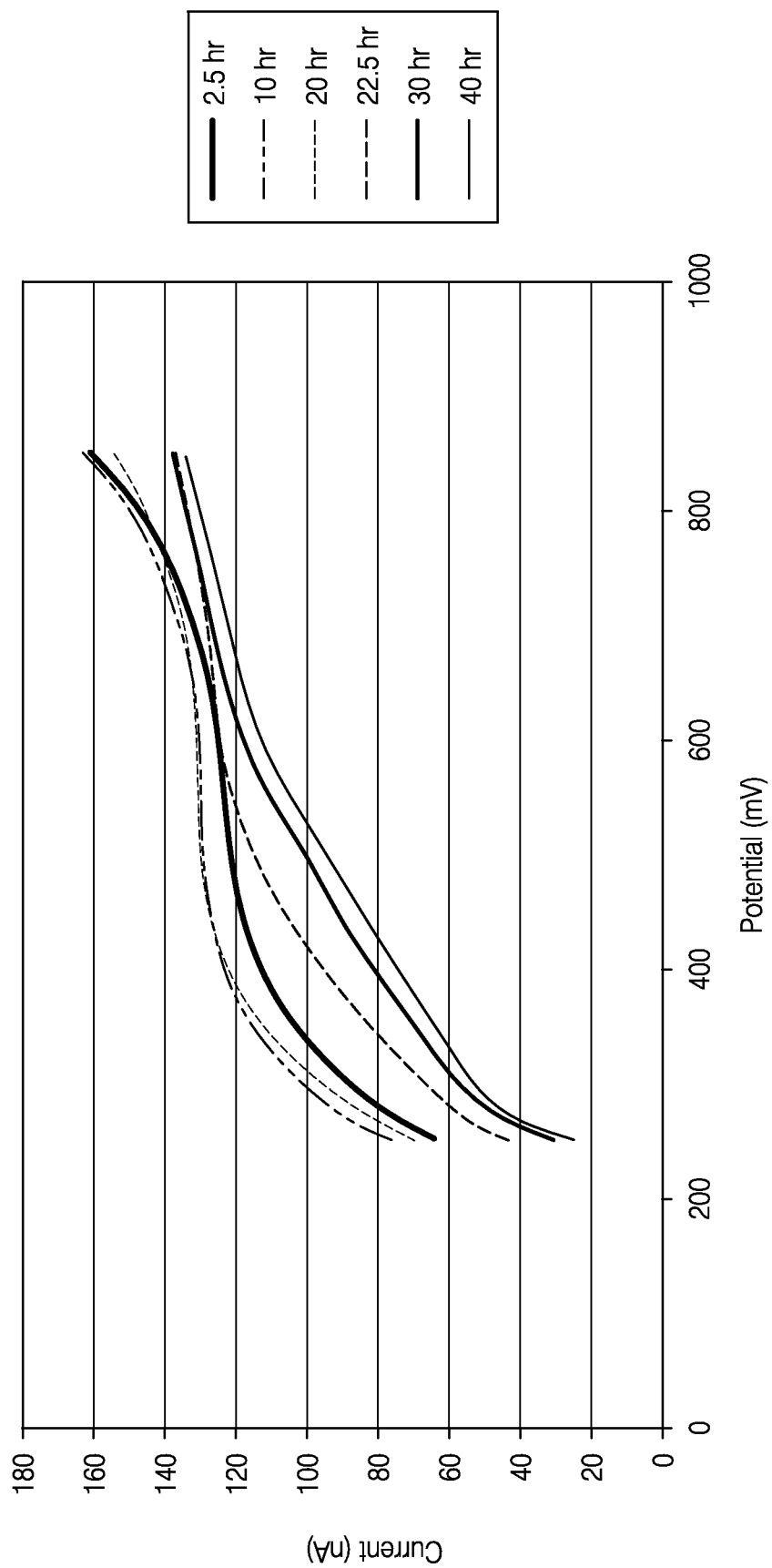
FIG. 11 illustrates plots that record pulse voltammetry conducted intermittently between 2.5 and 40 hours post sensor activation.

To identify this decrease in reference electrode capacity, in some embodiments, the glucose sensor is configured to perform voltammetry by periodically sweeping or scanning the bias potential and recording the signal response. In FIG. 11, pulse voltammetry is performed at about 2.5, 10, 20, 22.5, 30, and 40 hours after sensor activation. With each pulse voltammetry performed, a curved plot is obtained. Although pulsed voltammetry is used in the example illustrated in FIG. 11, it is to be understood that any of a variety of voltammetry techniques (e.g., cyclic voltammetry, squarewave voltammetry, and staircase voltammetry) may also be used in replacement of (or in addition) to pulse voltammetry. Certain sections of the plot may be more important than other others in terms of analysis for identifying an end of life event for the reference electrode. For example, for an electrochemical-based glucose sensor that employs a bias potential of about 600 mV and that measures glucose concentration by measuring oxidized hydrogen peroxide, the section of the plot near 600 mV may be important. In one embodiment, the end of life of a reference electrode can be identified when the most recent plot(s) have a shape or a shift in a certain section (e.g., the section around 600 mV) that is substantially different from those of other plots made during an earlier time. For example, in FIG. 11, at a section near a bias potential of 600 mV, the plots corresponding to 30 and 40 hour post sensor activation show a shift that is not insubstantial. In certain embodiments, the sensor system may be programmed to have a certain threshold corresponding to shift, such that if the shift exceeds such threshold, the possibility of an end of life event for the reference electrode is identified.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,559; 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S.

Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-

A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; U.S. Patent Publication No. 2005-0182451-A1; U.S. Patent Publication No. 2013000536650A1; and U.S. Patent Publication No. 2013-0053666-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS"; U.S. application Ser. No. 13/779,607 filed on Feb. 27, 2013 and entitled "ZWITTERION SURFACE MODIFICATIONS FOR CONTINUOUS SENSORS"; U.S. application Ser. No. 13/780,808 filed on Feb. 28, 2013 and entitled "SENSORS FOR CONTINUOUS ANALYTE MONITORING, AND RELATED METHODS"; U.S. application Ser. No. 13/784,523 filed on Mar. 4, 2013 and entitled "ANALYTE SENSOR WITH INCREASED REFERENCE CAPACITY"; U.S. application Ser. No. 13/789,371 filed on Mar. 7, 2013 and entitled "MULTIPLE ELECTRODE SYSTEM FOR A CONTINUOUS ANALYTE SENSOR, AND RELATED METHODS"; U.S. application Ser. No. 13/789,279 filed on Mar. 7, 2013 and entitled "USE OF SENSOR REDUNDANCY TO DETECT SENSOR FAILURES"; U.S. application Ser. No. 13/789,339 filed on Mar. 7, 2013 and entitled "DYNAMIC REPORT BUILDING"; U.S. application Ser. No. 13/789,341 filed on Mar. 7, 2013 and entitled "REPORTING MODULES"; U.S. application Ser. No. 13/790,281 filed on Mar. 8, 2013 and entitled "SYSTEMS AND METHODS FOR MANAGING GLYCEMIC VARIABILITY"; U.S. application Ser. No. 13/796,185 filed on Mar. 12, 2013 and entitled "SYSTEMS AND METHODS FOR PROCESSING ANALYTE SENSOR DATA"; U.S. application Ser. No. 13/796,642 filed on Mar. 12, 2013 and entitled "SYSTEMS AND METHODS FOR PROCESSING ANALYTE SENSOR DATA"; U.S. application Ser. No. 13/801,445 filed on Mar. 13, 2013 and entitled "SYSTEMS AND METHODS FOR LEVERAGING SMARTPHONE FEATURES IN CONTINUOUS GLUCOSE MONITORING"; U.S. application Ser. No. 13/802,424 filed on Mar. 13, 2013 and entitled "SYSTEMS AND METHODS FOR LEVERAGING SMARTPHONE FEATURES IN CONTINUOUS GLUCOSE MONITORING"; U.S. application Ser. No. 13/802,237 filed on Mar. 13, 2013 and entitled "SYSTEMS AND METHODS FOR LEVERAGING SMARTPHONE FEATURES IN CONTINUOUS GLUCOSE MONITORING"; U.S. application Ser. No. 13/802,317 filed on Mar. 13, 2013 and entitled "SYSTEMS AND METHODS FOR LEVERAGING SMARTPHONE FEATURES IN CONTINUOUS GLUCOSE MONITORING"; U.S. application Ser. No. 13/830,540 filed on Mar. 14, 2013 and entitled "TRANSCUTANEOUS ANALYTE SENSORS, APPLICATORS THEREFOR, AND ASSOCIATED METHODS"; U.S. application Ser. No. 13/829,722 filed on Mar. 14, 2013 and entitled "TRANSCUTANEOUS ANALYTE SENSORS, APPLICATORS THEREFOR, AND ASSOCIATED METHODS"; U.S. application Ser. No. 13/830,330 filed on Mar. 14, 2013 and entitled "SYSTEMS AND METHODS FOR PROCESSING AND TRANSMITTING SENSOR DATA"; U.S. application Ser. No. 13/827,577 filed on Mar. 14, 2013 and entitled "SYSTEMS AND METHODS FOR PROCESSING AND TRANSMITTING SENSOR DATA"; U.S. application Ser. No. 13/830,330 filed on Mar. 14, 2013 and entitled "SYSTEMS AND METHODS FOR PROCESSING AND TRANSMITTING SENSOR DATA"; and U.S. application Ser. No. 13/827,119 filed on Mar. 14, 2013 and entitled "ADVANCED CALIBRATION FOR ANALYTE SENSORS".

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method performed using a continuous glucose sensor, the method comprising:
   receiving sensor data generated by a continuous glucose sensor, wherein the sensor data is indicative of a concentration of glucose in a user;
   identifying, using a processor module, a post-implantation loss of sensitivity of the continuous glucose sensor, wherein identifying the post-implantation loss of sensitivity comprises:
      measuring a first impedance associated with the continuous glucose sensor at a first time point;
      measuring a second impedance associated with the continuous glucose sensor at a second time point, wherein the first time point is different than the second time point; and
      determining an occurrence of the post-implantation loss of sensitivity by comparing the first impedance measurement with the second impedance measurement;
   deactivating the continuous glucose sensor responsive to the determination of the occurrence of the post-implantation loss of sensitivity event;
   based on the comparing of the first impedance measurement and the second impedance measurement, determining that the post-implantation loss of sensitivity event is temporary; and
   after the continuous glucose sensor is deactivated, reactivating the continuous glucose sensor.

2. The method of claim 1, wherein the sensor data comprises data indicative of a signal response to at least one event selected from the group consisting of a signal response to cessation of blood flow to a site surrounding sensor implantation, a signal response to reduction of blood flow to a site surrounding sensor implantation, and a signal response to a vasospastic event.

3. The method of claim 1, wherein identifying the post-implantation loss of sensitivity further comprises:
   deactivating the continuous glucose sensor for a time period, whereby a product from a catalyzed reaction of glucose and oxygen accumulates over the time period;
   activating the continuous glucose sensor and measuring a signal value of the continuous glucose sensor immediately after the time period; and
   determining an occurrence of a post-implantation loss of sensitivity event if the signal value is greater than a predetermined value.

4. The method of claim 1, wherein identifying the post-implantation loss of sensitivity further comprises determining a pH of a biological fluid surrounding the continuous glucose sensor.

5. The method of claim 1, wherein identifying the post-implantation loss of sensitivity further comprises:
   measuring a concentration value of a non-glucose analyte; and
   determining an occurrence of a post-implantation loss of sensitivity event if the concentration value of the non-glucose analyte changes more than a predetermined amount.

6. The method of claim 1, wherein the continuous glucose sensor comprises a first electrode and a second electrode.

7. The method of claim 6, wherein the first electrode and second electrode have different dimensions.

8. The method of claim 7, wherein the second electrode is configured to have a dimension that positions the second electrode post-implantation outside of a site affected by cessation or reduction of blood flow.

9. The method of claim 6, wherein at least one of the first electrode and the second electrode is configured to minimize tissue trauma from implantation.

10. The method of claim 6, further comprising:
    determining that the second electrode is positioned outside of a site affected by cessation or reduction of blood flow; and
    wherein processing the sensor data responsive to the identification of the loss of sensitivity comprises according more weight to sensor data generated by the second electrode than sensor data generated by the first electrode.

11. The method of claim 1, wherein the post-implantation loss of sensitivity of the continuous glucose sensor is due to accumulation of biological material on a membrane of the continuous glucose sensor.

12. The method of claim 1, wherein the post-implantation loss of sensitivity of the continuous glucose sensor is due to a biological encapsulation of at least a portion of the continuous glucose sensor.

13. The method of claim 1, wherein the post-implantation loss of sensitivity is transient.

14. The method of claim 1, wherein the post-implantation loss of sensitivity of the continuous glucose sensor is due to a local cessation of blood flow in an implantation area.

\* \* \* \* \*

UNITED STATES PATENT AND TRADEMARK OFFICE
CERTIFICATE OF CORRECTION

PATENT NO. : 10,722,161 B2
APPLICATION NO. : 13/836260
DATED : July 28, 2020
INVENTOR(S) : Naresh C. Bhavaraju et al.

It is certified that error appears in the above-identified patent and that said Letters Patent is hereby corrected as shown below:

In the Specification

Column 8, Line 17, delete "andrenostenedione;" and insert -- androstenedione; --.

Column 8, Line 32, delete "diptheria" and insert -- diphtheria --.

Column 8, Line 39, delete "perioxidase;" and insert -- peroxidase; --.

Column 8, Line 48, delete "sissomicin;" and insert -- sisomicin; --.

Column 8, Line 52, delete "duodenalisa," and insert -- duodenalis, --.

Column 8, Line 60, delete "Trepenoma pallidium," and insert -- Treponema pallidum, --.

Column 8, Line 61, delete "stomatis" and insert -- stomatitis --.

Column 9, Lines 14-15, delete "(barbituates," and insert -- (barbiturates, --.

Column 9, Line 30, delete "(FHIAA)." and insert -- (5-HIAA). --.

Column 16, Lines 59-60, delete "analyte-measurement," and insert -- analyte measurement, --.

Column 36, Line 67, delete "electrode" and insert -- electrode. --.

Signed and Sealed this
Sixth Day of October, 2020

Andrei Iancu
*Director of the United States Patent and Trademark Office*